(12) United States Patent
Caylor, III et al.

(10) Patent No.: US 8,075,627 B2
(45) Date of Patent: Dec. 13, 2011

(54) SYSTEM AND METHOD FOR TRANSMITTING ORTHOPAEDIC IMPLANT DATA

(75) Inventors: Edward J. Caylor, III, Fort Wayne, IN (US); Mark R. DiSilvestro, Columbia City, IN (US); Jason T. Sherman, Leesburg, IN (US)

(73) Assignee: DePuy Products, Inc., Warsaw, IN (US)

( * ) Notice: Subject to any disclaimer, the term of this patent is extended or adjusted under 35 U.S.C. 154(b) by 1229 days.

(21) Appl. No.: 11/399,878

(22) Filed: Apr. 7, 2006

(65) Prior Publication Data

US 2007/0239282 A1    Oct. 11, 2007

(51) Int. Cl.
*A61F 2/38* (2006.01)
(52) U.S. Cl. ..................................... 623/20.34
(58) Field of Classification Search .......... None
See application file for complete search history.

(56) References Cited

U.S. PATENT DOCUMENTS

| | | |
|---|---|---|
| 4,352,960 A | 10/1982 | Dormer |
| 4,436,684 A | 3/1984 | White |
| 4,467,809 A | 8/1984 | Brighton |
| 4,549,547 A | 10/1985 | Brighton et al. |
| 4,830,021 A | 5/1989 | Thornton |
| 4,936,862 A | 6/1990 | Walker |
| 5,211,165 A | 5/1993 | Dumoulin et al. |
| 5,300,120 A | 4/1994 | Knapp et al. |
| 5,350,379 A | 9/1994 | Spievack |
| 5,356,411 A | 10/1994 | Spievack |
| 5,362,996 A | 11/1994 | Yizraeli |
| 5,383,915 A | 1/1995 | Adams |
| 5,448,489 A | 9/1995 | Reuben |
| 5,488,952 A | 2/1996 | Schoolman |
| 5,522,402 A | 6/1996 | Cooley |
| 5,536,269 A | 7/1996 | Spievack |
| 5,610,996 A | 3/1997 | Eller |
| 5,626,579 A | 5/1997 | Muschler et al. |
| 5,662,111 A | 9/1997 | Cosman |

(Continued)

FOREIGN PATENT DOCUMENTS

EP    1 570 782 A2    3/2005

(Continued)

OTHER PUBLICATIONS

European Search Report for European Application No. 07251541.4-2310, Aug. 16, 2007, 6 pages.

(Continued)

*Primary Examiner* — Thomas J Sweet
*Assistant Examiner* — Rebecca Straszheim
(74) *Attorney, Agent, or Firm* — Barnes & Thornburg LLP

(57) ABSTRACT

A system and method for transmitting implant data includes an orthopaedic implant, a wireless receiver, and a processing circuit electrically coupled to the wireless receiver. The orthopaedic implant is configured to transmit implant identification data and implant sensor data to the wireless receiver in response to a power signal. The orthopedic implant may transfer the data over, for example, a wireless network. The processing circuit receives the implant identification data and the implant sensor data from the wireless receiver and is configured to retrieve patient-related data from a database based on the implant identification data. The processing circuit may also be configured to update a patient queue, assign a patient room to a patient, and/or transmit the patient-related data and the implant sensor data to a client machine located in the patient room.

14 Claims, 13 Drawing Sheets

U.S. PATENT DOCUMENTS

| | | |
|---|---|---|
| 5,704,939 A | 1/1998 | Justin |
| 5,715,837 A | 2/1998 | Chen |
| 5,741,215 A | 4/1998 | D'Urso |
| 5,741,316 A | 4/1998 | Chen et al. |
| 5,798,924 A | 8/1998 | Eufinger et al. |
| 5,807,258 A | 9/1998 | Cimochowski et al. |
| 5,832,488 A | 11/1998 | Eberhardt |
| 5,855,609 A | 1/1999 | Knapp |
| 5,961,553 A | 10/1999 | Coty et al. |
| 6,002,859 A | 12/1999 | DiGioia et al. |
| 6,034,296 A | 3/2000 | Elvin et al. |
| 6,083,174 A | 7/2000 | Brehmeier-Flick et al. |
| 6,115,636 A | 9/2000 | Ryan |
| 6,126,690 A | 10/2000 | Ateshian et al. |
| 6,144,385 A | 11/2000 | Girard |
| 6,151,581 A | 11/2000 | Kraftson et al. |
| 6,161,080 A | 12/2000 | Aouni-Ateshian et al. |
| 6,177,034 B1 | 1/2001 | Ferrone |
| 6,239,705 B1 | 5/2001 | Glen |
| 6,254,639 B1 | 7/2001 | Peckitt |
| 6,336,929 B1 | 1/2002 | Justin |
| 6,366,799 B1 | 4/2002 | Acker et al. |
| 6,369,694 B1 | 4/2002 | Mejia |
| 6,400,272 B1 | 6/2002 | Holtzman et al. |
| 6,442,432 B2 | 8/2002 | Lee |
| 6,447,448 B1 | 9/2002 | Ishikawa et al. |
| 6,458,161 B1 | 10/2002 | Gibbs et al. |
| 6,459,943 B1 | 10/2002 | Suetani et al. |
| 6,474,599 B1 | 11/2002 | Stomski |
| 6,480,745 B2 | 11/2002 | Nelson et al. |
| 6,529,127 B2 | 3/2003 | Townsend |
| 6,559,620 B2 | 5/2003 | Zhou et al. |
| 6,565,576 B1 | 5/2003 | Stauch |
| 6,574,511 B2 | 6/2003 | Lee |
| 6,656,135 B2 | 12/2003 | Zogbi et al. |
| 6,674,883 B1 | 1/2004 | Wei et al. |
| 6,687,131 B1 | 2/2004 | Miehling |
| 6,700,547 B2 | 3/2004 | Mejia et al. |
| 6,720,930 B2 | 4/2004 | Johnson et al. |
| 6,750,866 B1 | 6/2004 | Anderson, III |
| 6,772,002 B2 | 8/2004 | Schmidt et al. |
| 6,793,496 B2 | 9/2004 | Edic et al. |
| 6,799,066 B2 | 9/2004 | Steines et al. |
| 6,804,558 B2 * | 10/2004 | Haller et al. ............ 607/30 |
| 6,833,790 B2 | 12/2004 | Mejia et al. |
| 6,847,892 B2 | 1/2005 | Zhou et al. |
| 6,947,004 B2 | 9/2005 | Mejia et al. |
| 7,015,826 B1 | 3/2006 | Chan et al. |
| 7,191,007 B2 | 3/2007 | Desai |
| 7,191,013 B1 | 3/2007 | Miranda et al. |
| 7,218,232 B2 | 5/2007 | DiSilvestro et al. |
| 7,599,743 B2 | 10/2009 | Hassler, Jr. et al. |
| 7,599,744 B2 | 10/2009 | Giordano et al. |
| 2001/0051787 A1 | 12/2001 | Haller et al. |
| 2002/0024450 A1 | 2/2002 | Townsend |
| 2002/0065539 A1 | 5/2002 | Von Arx et al. |
| 2002/0077562 A1 | 6/2002 | Kalgren et al. |
| 2002/0128872 A1 | 9/2002 | Giammattei |
| 2002/0135336 A1 | 9/2002 | Zhou et al. |
| 2002/0151770 A1 * | 10/2002 | Noll et al. ............ 600/300 |
| 2002/0198740 A1 | 12/2002 | Roman |
| 2003/0045787 A1 | 3/2003 | Schulze |
| 2003/0067736 A1 | 4/2003 | Vahamaki et al. |
| 2003/0069644 A1 | 4/2003 | Kovacevic |
| 2003/0154411 A1 | 8/2003 | Hovik |
| 2004/0008123 A1 | 1/2004 | Carrender et al. |
| 2004/0011137 A1 | 1/2004 | Hnat et al. |
| 2004/0019384 A1 | 1/2004 | Kirking et al. |
| 2004/0030395 A1 | 2/2004 | Blunn et al. |
| 2004/0078219 A1 * | 4/2004 | Kaylor et al. ............ 705/2 |
| 2004/0113790 A1 * | 6/2004 | Hamel et al. ............ 340/572.1 |
| 2004/0138663 A1 | 7/2004 | Kosashvili |
| 2004/0138925 A1 | 7/2004 | Zheng |
| 2004/0171924 A1 | 9/2004 | Mire et al. |
| 2004/0178955 A1 | 9/2004 | Menache et al. |
| 2004/0230226 A1 | 11/2004 | Bingham |
| 2005/0010299 A1 | 1/2005 | Disilvestro |
| 2005/0010300 A1 * | 1/2005 | Disilvestro et al. ........ 623/18.12 |
| 2005/0027330 A1 | 2/2005 | Govari |
| 2005/0055316 A1 | 3/2005 | Williams |
| 2005/0065815 A1 | 3/2005 | Mazar |
| 2005/0075697 A1 | 4/2005 | Olson et al. |
| 2005/0091338 A1 | 4/2005 | de la Huerga |
| 2005/0099290 A1 | 5/2005 | Govari |
| 2005/0101962 A1 | 5/2005 | Schwenke |
| 2005/0113887 A1 | 5/2005 | Bauhahn |
| 2005/0119716 A1 | 6/2005 | McClure et al. |
| 2005/0165317 A1 | 7/2005 | Turner et al. |
| 2005/0288739 A1 | 12/2005 | Hassler |
| 2005/0288740 A1 | 12/2005 | Hassler |
| 2005/0288741 A1 | 12/2005 | Hassler |
| 2006/0009856 A1 | 1/2006 | Sherman |
| 2006/0030945 A1 | 2/2006 | Wright |
| 2006/0074319 A1 | 4/2006 | Barnes et al. |
| 2006/0136013 A1 | 6/2006 | Sherman |
| 2006/0190080 A1 | 8/2006 | Danoff |
| 2007/0005141 A1 | 1/2007 | Sherman |
| 2007/0179627 A1 | 8/2007 | Gustilo et al. |
| 2007/0239282 A1 | 10/2007 | Caylor et al. |
| 2008/0065225 A1 * | 3/2008 | Wasielewski et al. ..... 623/18.11 |

FOREIGN PATENT DOCUMENTS

| | | |
|---|---|---|
| EP | 1 571 581 A1 | 3/2005 |
| EP | 1 611 835 A2 | 6/2005 |
| EP | 1 671 577 A1 | 12/2005 |
| GB | 2 239 802 A | 7/1991 |
| GB | 2 382 777 A | 6/2003 |
| WO | 99/56614 A1 | 11/1999 |
| WO | 00/13585 A1 | 3/2000 |
| WO | 0013585 | 3/2000 |
| WO | 01/37926 A1 | 5/2001 |
| WO | 0149173 | 7/2001 |
| WO | 02/080753 A2 | 10/2002 |
| WO | 02/091399 A1 | 11/2002 |
| WO | 02/094113 A1 | 11/2002 |
| WO | 2004/026399 A1 | 4/2004 |
| WO | 2005/084544 A1 | 9/2005 |
| WO | 2005120203 | 12/2005 |

OTHER PUBLICATIONS

European Search Report for European Application No. 07251541.4-2310, Nov. 5, 2007, 9 pgs.

Want, Roy, "RFID a Key to Automating Everything," *Scientific American*, Jan. 2004, pp. 56-65, (13 pages).

D'Lima et al., 2005, "An implantable telemetry device to measure intra-articulartibial forces", Journal of Biomechanics, 38 pages 299-304 (6 pages).

Graichen et al., 1999, "Implantable Telemetry System for Measurement of Hip Joint Force and Termperature", 15th Int. Symposium of Biotelemetry, Juneau, Alaska, US (Abstract).

European Search Report for EP 10174347.4-2310 dated Nov. 4, 2010 (6 pages).

* cited by examiner

SYSTEM AND METHOD FOR TRANSMITTING ORTHOPAEDIC IMPLANT DATA

CROSS-REFERENCE TO RELATED U.S. PATENT APPLICATION

Cross-reference is made to U.S. Utility patent application Serial No. 11/400,095 entitled "System and Method for Managing Patient-Related Data," which was filed Apr. 7, 2006 by Mark R. DiSilvestro et al., the entirety of which is expressly incorporated herein by reference.

TECHNICAL FIELD

The present disclosure relates generally to systems and methods for managing patient-related data.

BACKGROUND

Prior to a medical examination, surgical, or other medical appointment, a patient must typically register with a receptionist or other personnel of the doctor's office or hospital wherein the examination or surgical procedure will be performed. During the registration process, the patient may be required to supply or verify information related to his or her identify and/or medical history. The receptionist uses the information supplied by the patient to manually retrieve medical records physically stored at the doctor's office or hospital and/or stored on the doctor's office or hospital's network. The patient is typically required to provide any additional information required for the medical examination or surgical procedure.

The patient is also typically required to "sign-in" on a patient list, which is manually updated by the receptionist as patient examinations or surgical procedures are completed and patient rooms become available. Once a patient room is available for the new patient, the receptionist or other caregiver notifies the patient and manually transfers the retrieved medical records to the assigned patient room for the doctor's review.

SUMMARY

According to one aspect, an orthopaedic implant includes a housing having an aperture defined therein and a secondary coil positioned in the aperture. The secondary coil may include a number of turns positioned so as to define a reference plane. The reference plane may be substantially parallel to a sagittal plane of a body of a patient with the orthopaedic implant is implanted in the patient. The orthopedic implant may be, for example, a tibial tray. The orthopaedic implant may also include a processing circuit electrically coupled to the secondary coil. The processing circuit may be configured to receive a power signal from the secondary coil when the secondary coil is inductively coupled with a primary coil. The orthopaedic implant may also include a wireless transmitter coupled to the processing circuit and an antenna coil electrically coupled to the wireless transmitter. The processing circuit may be configured to control the wireless transmitter to transmit implant identification data in response to the power signal using the antenna coil. The orthopaedic implant may also include one or more sensors such as, for example, a pressure sensor, a load sensor, a temperature sensor, and/or a hall-effect sensor. The processing circuit may be configured to receive an output signal from the sensor(s) and control the wireless transmitter to transmit the output signal in response to the power signal using the antenna coil. The transmitter may be configured to transmit the implant identification data and/or the output data using a wireless local area network frequency. For example, the transmitter may transmit the implant identification data and/or the output data at a frequency of about 2.4 gigahertz. Additionally or alternatively, the transmitter may transmit such data using a Bluetooth transmission protocol.

According to another aspect, a method for transmitting data from an orthopaedic implant includes receiving a power signal generated by a primary coil with a secondary coil of the orthopaedic implant. For example, the secondary coil may receive the power signal by transcutaneously receiving an amount of energy from the primary coil. The power signal may, for example, power a processing circuit and/or transmitter of the orthopaedic implant. The method may also include receiving an output signal from a sensor of the orthopaedic implant in response to the power signal. The sensor may be, for example, a pressure sensor, a load sensor, a temperature sensor, and a hall-effect sensor. The method may further include wirelessly transmitting implant identification data and the output signal in response to the power signal. The implant identification data and the output signal may be transmitted using a wireless local area network frequency such as, for example, a frequency of about 2.4 gigahertz. Additionally or alternatively, the implant identification data and the output signal may be transmitted using a Bluetooth transmission protocol. The implant identification data and the output signal may be transmitted to a wireless router.

According to a further aspect, a system for managing patient-related data may include an orthopaedic implant having a secondary coil, a primary coil, and a wireless receiver. The orthopaedic implant may be configured to transmit implant identification data and implant sensor data in response to a power signal. For example, the orthopaedic implant may be configured to transmit the implant identification data and the implant sensor data using a wireless local area network frequency such as, for example, a frequency of about 2.4 gigahertz. Additionally or alternatively, the orthopaedic implant maybe configured to transmit the implant identification data and the implant sensor data using a Bluetooth transmission protocol. The primary coil may be configured to inductively couple with a secondary coil of the orthopaedic implant to provide the power signal to the orthopaedic implant. The primary coil may be coupled, for example, coupled to a gate configured to allow patients to travel therethrough. The wireless receiver configured to receive the implant identification data and the implant sensor data transmitted by the orthopaedic implant. The wireless receiver may be, for example, a wireless router.

The system may also include a processor coupled to the wireless receiver and a memory device electrically coupled to the processor. The memory device may have stored therein a plurality of instructions, which when executed by the processor, cause the processor to receive the implant identification data and the implant sensor data from the wireless receiver and retrieve patient-related data from a database based on the implant identification data. For example, the processor may retrieve the patient-related data from a database of a hospital network. The plurality of instructions may further cause the processor to update an electronically-stored patient queue based on the retrieving step. Additionally, the plurality of instructions may further cause the processor to assign a patient room to a patient identified by the patient-related data based on the electronically-stored patient queue. The plurality of instructions may also cause the processor to transmit the patient-related data and the output sensor data to a client machine located in the patient room. The plurality of instructions may yet further cause the processor to determine the availability of the patient room based on the electronically-stored patient queue and provide an electronic notification if the patient room is available. For example, the processor may activate a public address system or display a name of a patient identified by the patient-related data on a display screen. The plurality of instructions may also cause the processor to transmit the patient-related data and the implant sensor data to a client machine and/or a portable media device over a wireless network.

BRIEF DESCRIPTION OF THE DRAWINGS

The detailed description particularly refers to the following figures, in which:

FIG. 5b is a cross-sectional, anterior-to-posterior view of the secondary coil assembly of FIG. 5a;

DETAILED DESCRIPTION OF THE DRAWINGS

Figure 1:
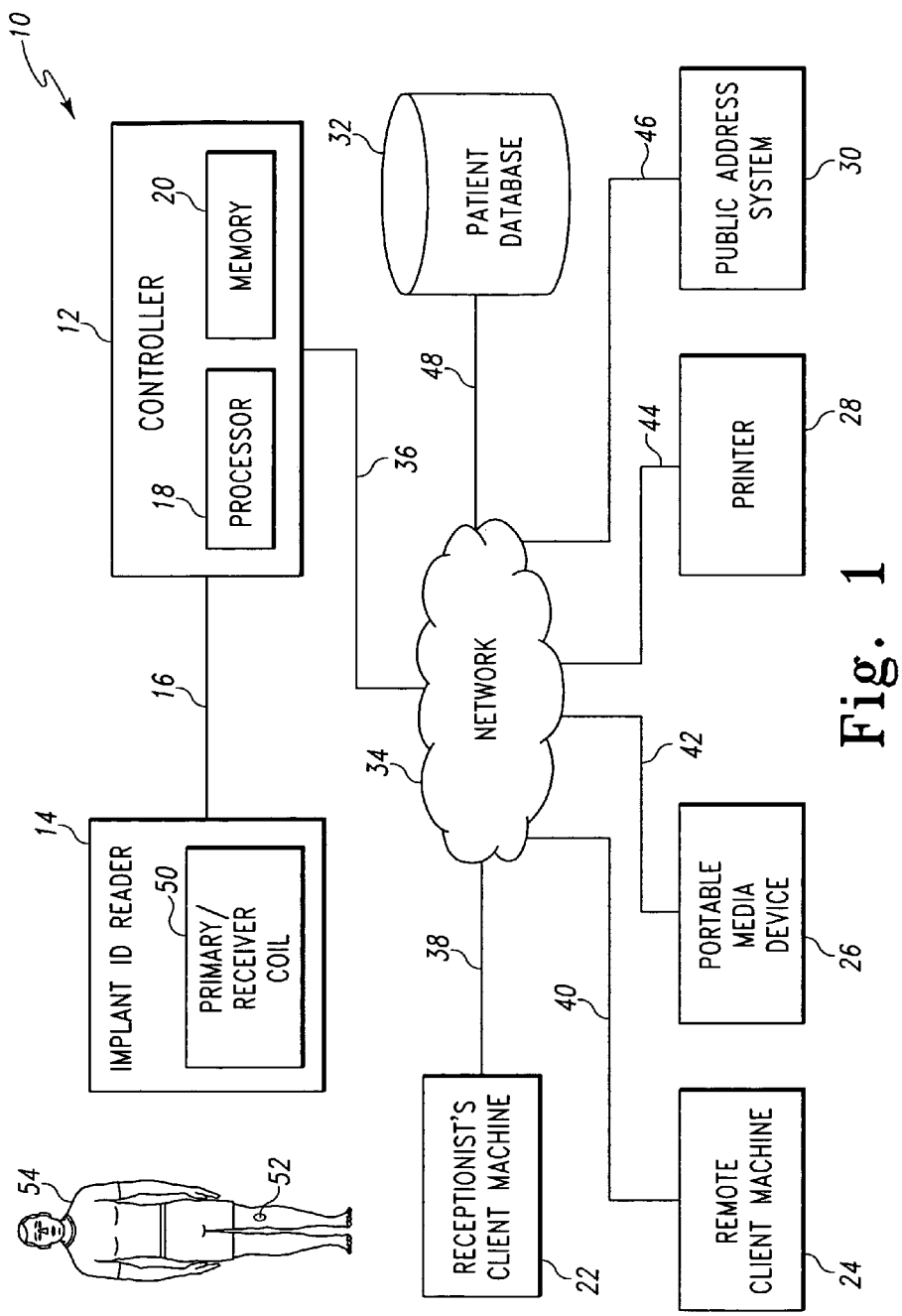
FIG. 1 is a simplified block diagram of a system for managing patient-related data.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a system 10 for managing patient-related data includes a controller 12 communicatively coupled to an implant identification reader 14 via a communication link 16. The controller 12 illustratively includes a processor 18 and a memory device 20. The processor 18 may be embodied as any type of processor including, for example, discrete processing circuitry (e.g., a collection of logic devices), general purpose integrated circuit(s), and/or application specific integrated circuit(s) (i.e., ASICs). The memory device 20 may be embodied as any type of memory device and may include one or more memory types, such as, random access memory (i.e., RAM) and/or read-only memory (i.e., ROM). In addition, the controller 12 may include other devices and circuitry typically found in a computer for performing the functions described herein such as, for example, a hard drive, input/output circuitry, and the like.

The controller 12 is communicatively coupled to a number of client machines 22, 24 via a network 34. The client machines 22, 24 may be embodied as any type of computer or computing device capable of displaying data to a user and receiving input from the user. For example, the client machines 22, 24 may be embodied as "dumb terminals" and include a display device, an input device such as a keyboard, and minimal peripherals. Alternatively, one or more of the client machines 22, 24 may be embodied as a typical desktop or laptop computer equipped with a display screen, keyboard, and other devices and circuitry typically found in a desktop and/or laptop computer. Illustratively, the system 10 includes one or more receptionists client machines 22 and one or more remote client machines 24. The receptionist's client machines 22 are located in the reception area of the doctor's office or hospital wherein the system 10 is incorporated and usable by a receptionist or nurse to monitor a patient queue, patient room availability, and the like.

Each of the remote client machines 24 may be located in a patient room such as a patient examination room or operating room of the doctor's office or hospital wherein the system 10 is incorporated. Additionally or alternatively, a remote client machine 24 may be located outside each patient room, in the doctor's or other caregiver's office, or in any other location of the doctor's office or hospital. The remote client machines 24 may be used by the doctors, nurses, or other caregivers to review and update patient-related data prior to, during, or subsequent to the examination, surgery, or other medical procedure. As used herein, the term patient-related data refers to any data related to a particular patient and may include, but is not limited to, patient medical records, X-rays, patient identification data, or the like.

The controller 12 is also coupled to one or more portable media devices 26 via the network 34. The portable media devices 26 may be embodied as any device capable of receiving data from the controller 12 and displaying such data to a user of the device 26. For example, the portable media device may be embodied as a personal digital assistant (PDA), portable laptop computer, or the like. The portable media device 26 may also be configured to receive input data from the user and transfer such data to the controller 12. As such, the portable media devices 26 may be used by the doctors, nurses, and/or other caregivers of the doctor's office or hospital wherein the system 10 is incorporated to remotely receive and/or transmit data to the controller 12.

The controller 12 is additionally coupled to one or more printers 28, a public address system 30, and a patient database 32 via the network 34. The printer(s) 28 may be any type of printer controllable by the controller 12. For example, the printer may be embodied as a dot-matrix printer, a ink jet printer, a laser printer, or the like. The printer(s) 28 may be located in the reception area of the doctor's office or hospital such that the printer 28 is accessible by the receptionist. Additionally or alternatively, one or more of the printers 28 may be located in a doctor's office or any other location wherein a printed copy of data may be required.

The public address system 30 may be embodied as any type of system capable of providing information to the patients of the doctor's office or hospital wherein the system 10 is incorporated. The public address system 30 may be embodied as a visual public address system, an audible address system, or a combination thereof. For example, the public address system 30 may be embodied as a loudspeaker located in a waiting area of the doctor's office or hospital. Additionally or alternatively, the public address system 30 may be embodied as a large display screen located in or viewable from the waiting area.

The patient database 32 may be embodied as any type of database capable of storing patient-related data. Although illustrated in FIG. 1 as a single database, it should be appreciated that the patient database 32 may be embodied as any number of separate databases, file folders, flat files, or other storage locations. As discussed in more detail below in regard to FIG. 10, the patient-related data stored in the database 32 is stored in association with, indexed by, or otherwise retrievable based on implant identification data. The patient database 32 may be located in the doctor's office or hospital wherein the system 10 is incorporated or may be located remotely therefrom. In one particular embodiment, the patient database 32 forms a portion of a hospital network that is accessible by the controller 12 via the network 34.

The network 34 may be embodied as any type of network capable of facilitating communication between the controller 12 and the client machines 22, 24, the portable media devices 26, the printers 28, the public address system 30, and the patient database 32. For example, the network 34 may be a local area network (LAN), a wide area network (WAN), or form a portion of a publicly-accessible, global network such as the Internet. In addition, the network 34 may be a wired network, a wireless network, or a combination thereof. The controller 12 is communicatively coupled to the network 34 via a communication link 36. The client machines 22, 24 are coupled to the network 34 via communication links 38, 40, respectively. The portable media devices 26 are communicatively coupled to the network 24 via communication links 42. The printers 28 and the public address system 30 are communicatively coupled to the network 34 via communication links 44, 46, respectively. Additionally, the patient database 32 is communicatively coupled to the network 34 via communication links 48. The communication links 36, 38, 40, 42, 44, 46, and 48 may be any type of communication link capable of facilitating communication between the controller 12 and the client machines 22, 24, the portable media devices 26, the printers 28, the public address system 30, and the patient database 32. For example, the communication links 36, 38, 40, 42, 44, 46, and 48 may be embodied as any number of wires, cables such as fiber optic cables, or the like. Additionally, any one or more of the communication links 36, 38, 40, 42, 44, 46, and 48 may be embodied as wired or wireless communication links. In embodiments wherein the communication links 36, 38, 40, 42, 44, 46, and 48 are wireless communication links, the controller 12, the client machines 22, 24, the portable media devices 26, the printers 28, the public address system 30, and/or the patient database 32 may include a wireless transmitter and/or receiver to facilitate wireless communication with the network 34.

The implant identification reader 14 includes a primary/receiver coil 50. The primary/receiver coil 50 is configured to be inductively coupled to a secondary coil of an orthopaedic implant 52 located in a patient 54 as discussed in more detail below in regard to FIGS. 2-5. The primary/receiver coil 50 may be any type of coil capable of generating an electromagnetic field to transcutaneously transfer an amount of energy to the orthopaedic implant and receive data therefrom. The implant identification reader 14 may be located at an entrance of the doctor's office or hospital wherein the system 10 is incorporated. The primary/receiver coil 50 is positioned in the implant identification reader 14 such that the orthopaedic implant 52 is positioned within the electromagnetic field generated by the primary receiver coil 50 when the patient 54 walks by the implant identification reader 14.

In use, the controller 12 energizes the primary/receiver coil 50 by supplying a power signal to the primary/receiver coil 50 via the communication link 16. The controller 12 may energize the primary/receiver coil 50 continuously, periodically, or in response to the presence of the patient 54. For example, a motion or load sensor may be located near the implant identification reader 14 to sense the presence of the patient 54. When the sensor detects that the patient 54 is near the implant identification reader 14, the sensor may transmit a output signal to the controller 12. In response to the output signal, the controller 12 may be configured to transmit the power signal to the primary/receiver coil 50 to cause the primary/receiver coil 50 to generate the electromagnetic field and thereby inductively couple with the secondary coil of the orthopaedic implant 52. In response to the electromagnetic field, the orthopaedic implant 52 is configured to transmit implant identification data as discussed below in regard to FIG. 9. The implant identification data may be embodied as any type of data that uniquely identifies the orthopaedic implant 52. For example, the implant identification data may be embodied as a code or password. The implant identification data is received by the primary/receiver coil 50 of the implant identification reader 14 and transmitted to the controller 12 via the communication link 16. In response to the implant identification data, the controller 12 is configured to retrieve patient-related data. As discussed in more detail below in regard to FIG. 10a-c, the controller 12 may also be configured to transmit the patient-related data to the client machines 22, 24 and/or the portable media device 26, control the printer 28 to print a patient information form to update the patient-related data, and/or control the public address system 30 to notify the patient when a patient room is available.

Figure 2:
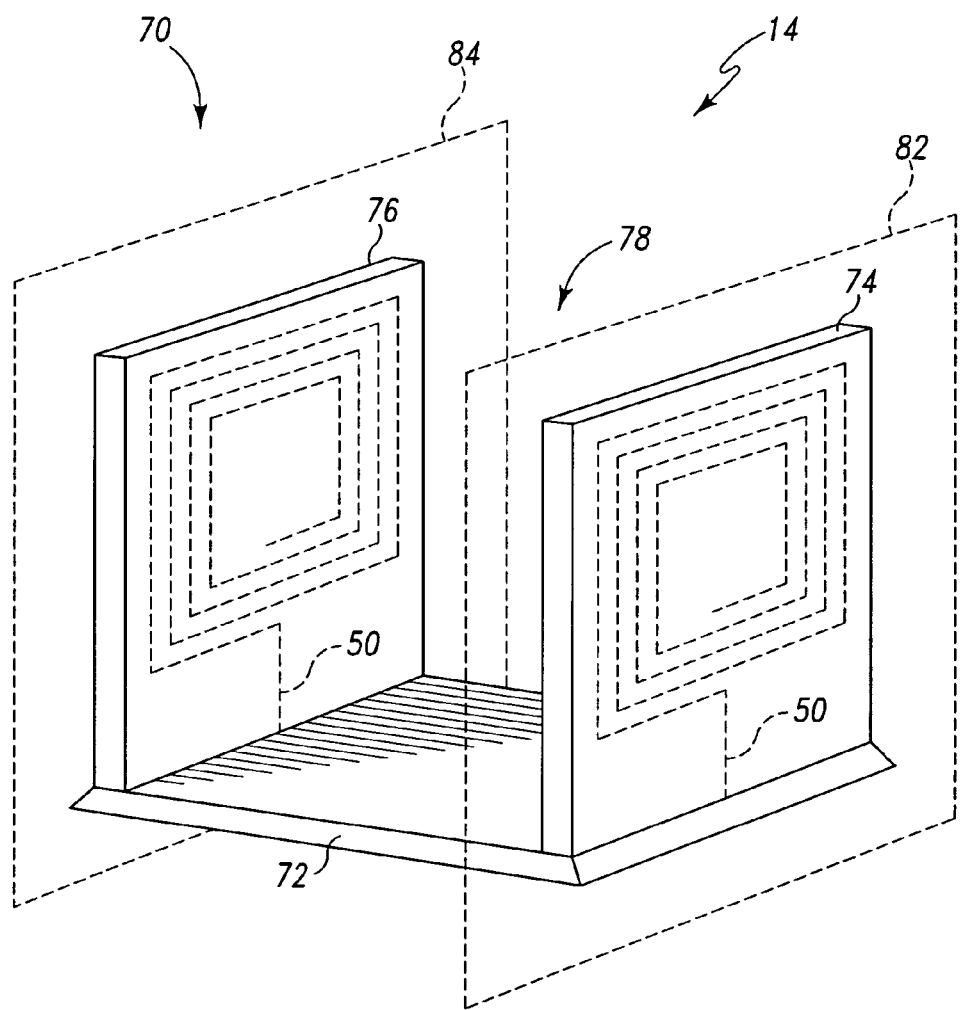
FIG. 2 is a perspective view of an implant identification reader of the system of FIG. 1.
Figure 3:
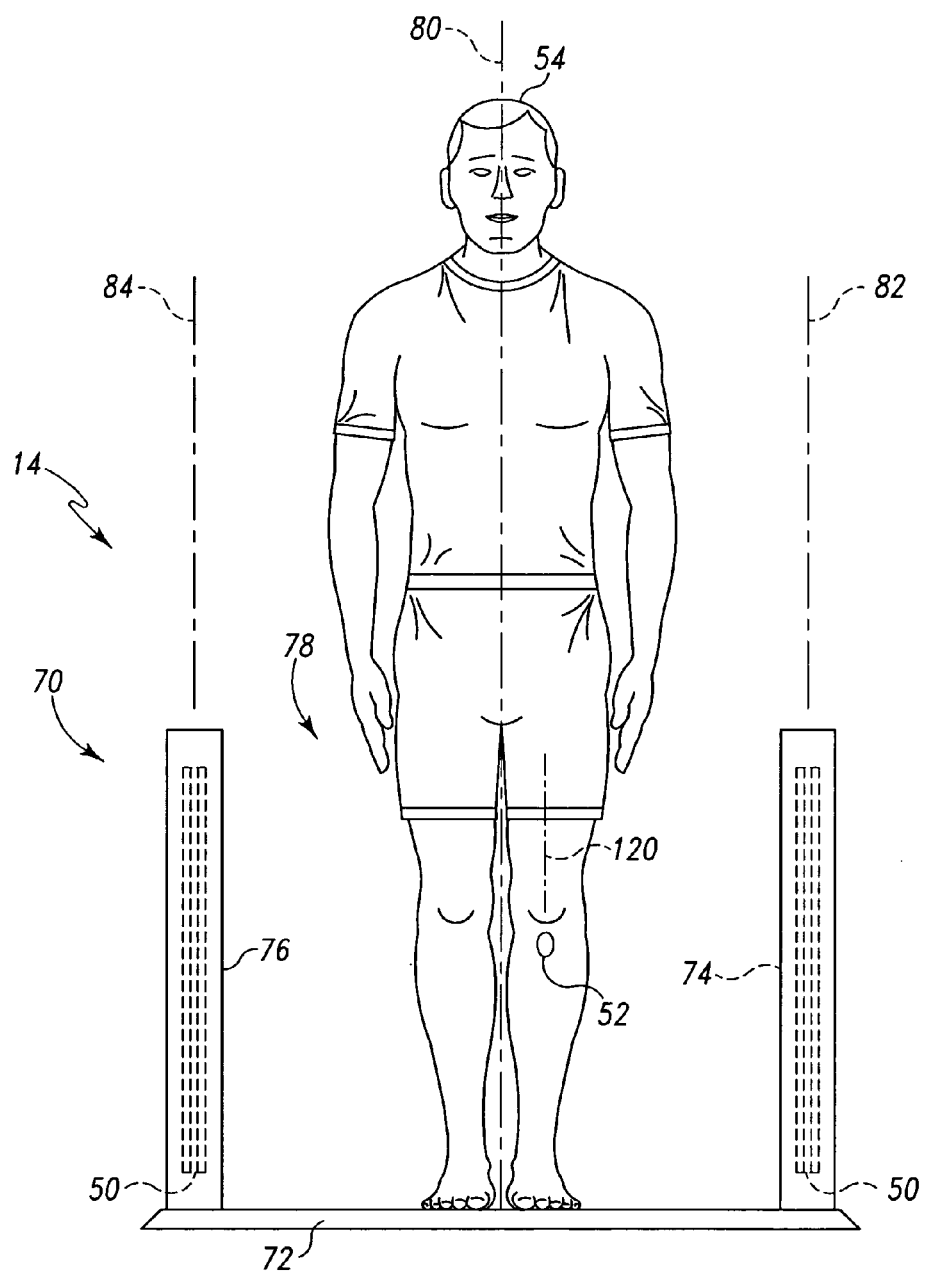
FIG. 3 is a elevated from view of the implant identification reader of FIG. 2.
Figure 4:
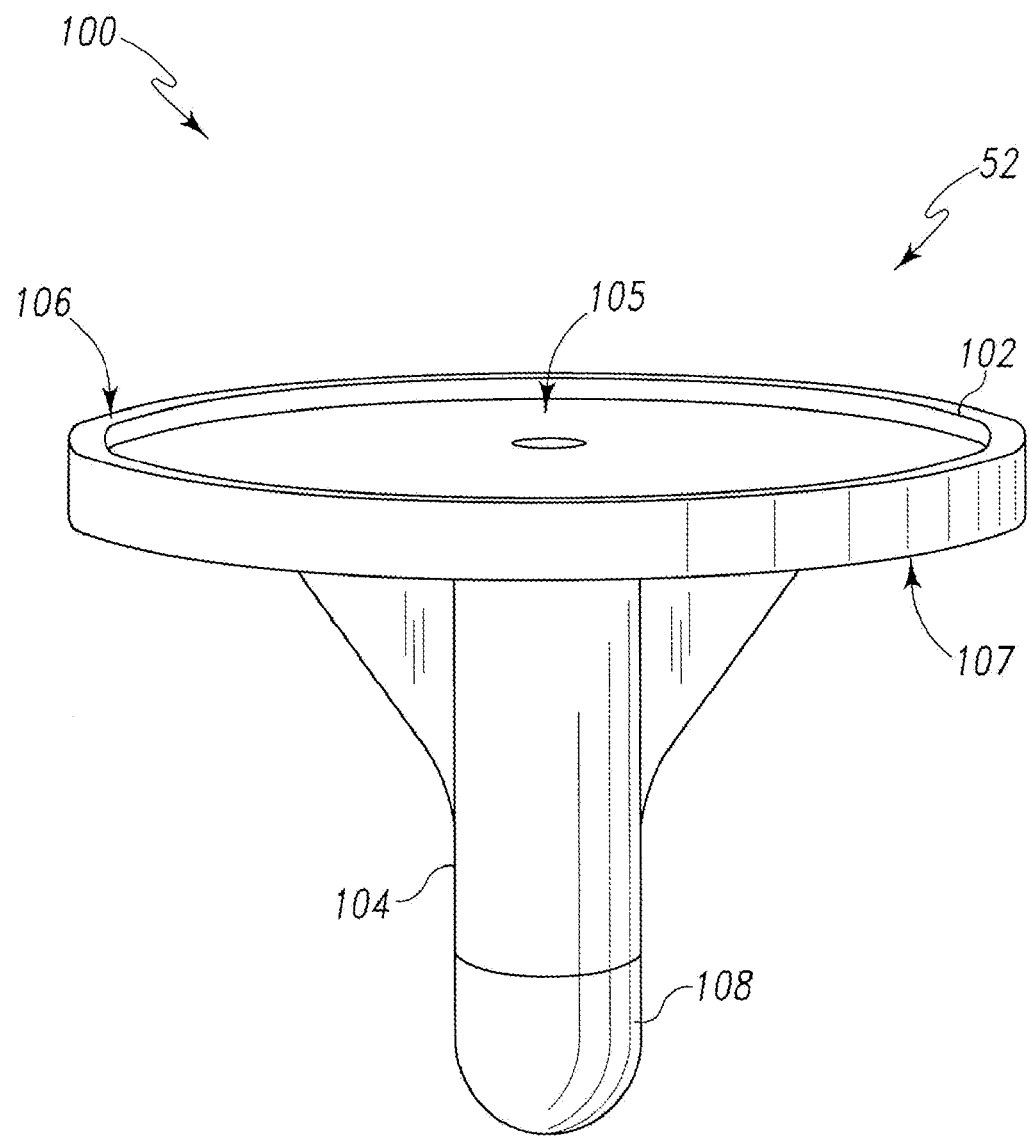
FIG. 4 is a perspective view of an orthopaedic implant usable with the system of FIG. 1.

Referring now to FIGS. 2 and 3, in one illustrative embodiment, the implant identification reader 14 is embodied as a gate 70. The gate 70 includes a base 72, a first side wall 74, and a second side wall 76. The first and second side walls 74, 76 define a passageway 78 therebetween. The gate 70 is configured to be located near an entrance of the doctor's office or hospital wherein the system 10 is incorporated such that the patient 54 is required to walk through the passageway 78 when the patient 54 enters the office or hospital. In the illustrative gate 70, a primary/receiver coil 50 is positioned in each of the side walls 74, 76. However, in other embodiments, only one of the side walls 74, 76 may include a primary/receiver coil 50. The primary/receiver coils 50 are embodied as spiral coils such that the turns of the coils 50 are located in reference planes 82, 84. The primary/receiver coils 50 are positioned in the side walls 74, 76 such that the reference planes 82, 84 are substantially parallel with a sagittal plane 80 of the patient 54 when the patient 54 walks through the passageway 78.

Referring now to FIGS. 4 and 5a-5d, in one illustrative embodiment, the orthopaedic implant 52 may be embodied as a tibial tray 100. The tibial tray 100 includes a platform 102 and a stem 104 configured to be implanted in a tibia bone of the patient 54. The platform 102 includes a top surface 106 having an aperture 105 configured to receive a polymer bearing (not shown) and a bottom surface 107. A secondary coil housing 108 is coupled to a distal end of the stem 104. The housing 108 may be formed from any suitable material which does not interfere with the functioning of the circuitry (e.g., the secondary coil and other circuitry as described below) included therein such as a polymer material. The housing 108 may be coupled to the stem 104 using any suitable coupling mechanism. For example, the housing 108 may include a screw portion 112 (see FIGS. 5a-5d) configured to be mated with a threaded aperture defined in the stem 104. Alternatively, the housing 108 may be coupled to stem 104 via a twist-lock mechanism. Moreover, in some embodiments, the housing 108 may be coupled to the stem 104 via any suitable type of adhesive or the like.

Figure 5A:
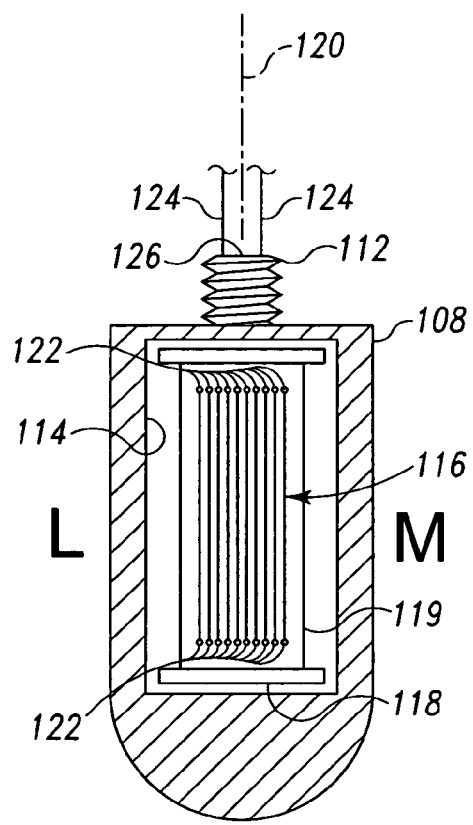
FIG. 5a is a cross-sectional, lateral-to-medial view of one embodiment of a secondary coil assembly of the orthopaedic implant of FIG. 4.
Figure 5B:
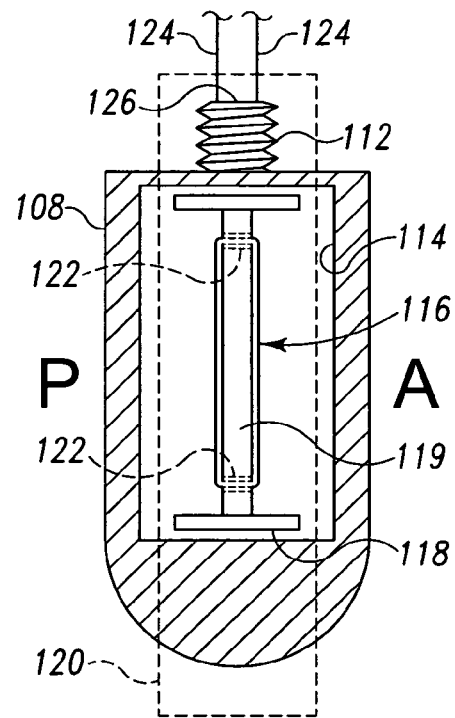

The housing 108 includes an aperture 114 defined therein. A secondary coil 116 is positioned in the aperture 114. In one embodiment, as illustrated in FIGS. 5a and 5b, the secondary coil 116 is secured to a bobbin 118 which is position in the chamber 114 and secured to the housing 108 in a fixed position. The bobbin 118 may be secured to the housing 108 in the chamber 114 using any suitable securing means such as, for example, press-fitting, an adhesive, securing devices such as screws or bolts, or the like.

The secondary coil 116 is formed from a number of coil turns defined on a coil receiving portion 119 of the bobbin 118. The illustrative bobbin 118 has a substantial "I" shape and includes a number apertures 122 through which the coil turns of the secondary coil 116 pass such that the secondary coil 116 may be formed from any number of coil turns. The coil turns of the secondary coil 116 are formed on the bobbin 118 such that the coil turns are located in a reference plane 120. The secondary coil 116 also includes coil terminal ends 124 that extend from the housing 108 via a passageway (not shown) defined in the screw portion 112. The secondary coil 116 is electrically coupled to electronic circuitry via the coil terminal ends 124 as discussed below in regard to FIGS. 6 and 7. Alternatively, the secondary coil 116 may be electrically coupled to electronic circuitry via two or more contacts (not shown) established on a top surface 126 of the screw portion 112. The contacts may be configured to mate with similar contacts established on the stem 104 when the housing 108 is coupled thereto. The electronic circuitry may be coupled to the contacts of the stem 104 such that the electronic circuitry is electrically coupled to the secondary coil 116 via the mated contacts when the housing is coupled to the stem 104. Such electronic circuitry may be positioned in a suitable aperture of the stem 104 and/or the platform 102. Additionally or alternatively, a portion of the electronic circuitry may be positioned in the housing 108 with the secondary coil 116.

In the embodiment illustrated in FIGS. 5a and 5b, the bobbin 118 is positioned and secured in the stem 104 of the tibial tray 100 such that the reference plane 120 formed from the coil turns of the secondary coil 116 are substantially parallel with the sagittal plane 80 of the patient 54 when the tibial tray 100 is properly implanted in the patient 54. In such a configuration, as illustrated in FIG. 3, when the patient 54 passes through the passageway 78 of the gate 70, the reference plane 120 defined by the coil turns of the secondary coil 116 of the orthopaedic implant 52 (e.g., the tibial tray 100) is substantially parallel with the reference planes 82, 84 defined by the coil turns of the primary/receiver coils 50. As such, because the secondary coil 116 and the primary/reference coil 50 are substantially parallel, the inductive coupling of the coils 50, 116 may be improved.

Figure 5C:
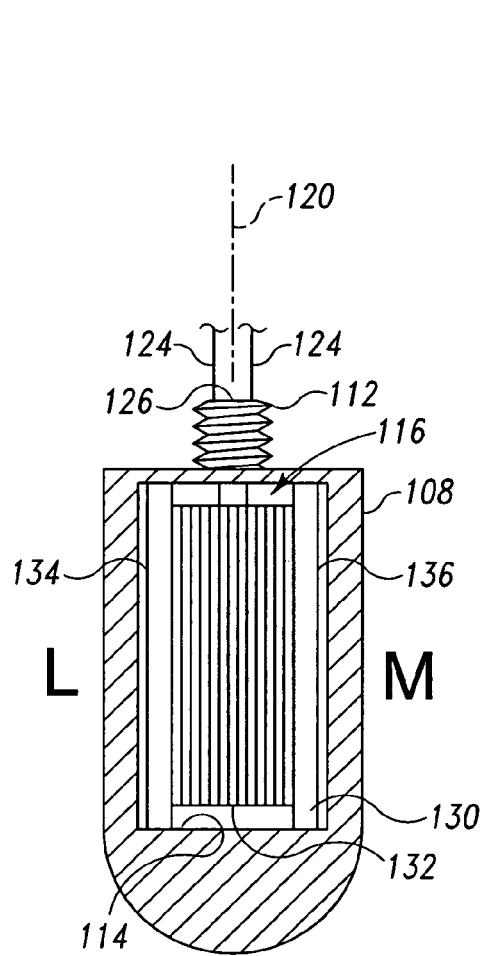
FIG. 5c is a cross-sectional, lateral-to-medial view of another embodiment of a secondary coil assembly of the orthopaedic implant of FIG. 4.

Alternatively, as illustrated in FIG. 5c, the secondary coil 116 is secured to a bobbin 130 that is positioned in the chamber 114. Similar to bobbin 118, the bobbin 130 may positioned in the chamber 114 and secured to the housing 108 using any suitable securing means such as, for example, press-fitting, an adhesive, securing devices such as screws or bolts, or the like. The bobbin 130 has a substantial circular cross-section and includes a round coil receiving portion 132 defined between a first and second end plate 134, 136. The coil turns of the secondary coil 116 are formed on the coil receiving portion 132 such that the coil turns are located in the reference plane 120. Similar to the bobbin 118 described above in regard to FIGS. 5a and 5b, the bobbin 130 is positioned and secured in the chamber 114 of the housing 108 such that the reference plane 120 formed from the coil turns of the secondary coil 116 are substantially parallel with the sagittal plane 80 of the patient 54 when the tibial tray 100 is properly implanted in the patient 54. Although the illustrative coil receiving portion 132 has a substantial round shape, it should be appreciated that in other embodiments, bobbins having any coil receiving portions of any shape may be used. For example, bobbins having oval, square, and/or rectangular coil receiving portions may be used.

Figure 5D:
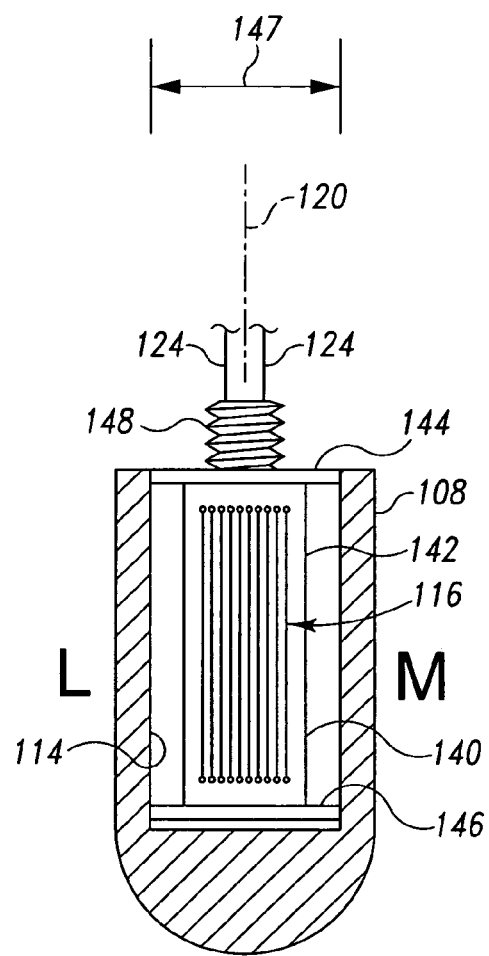
FIG. 5d is a cross-sectional, lateral-to-medial view of another embodiment of a secondary coil assembly of the orthopaedic implant of FIG. 4.

In another embodiment, as illustrated in FIG. 5d, the secondary coil 116 is secured to a bobbin 140 that is positioned in the chamber 114. The bobbin 140 includes a coil receiving portion 142 similar to the coil receiving portion 119 of the bobbin 118. The bobbin 140 also includes first and second end plates 144, 146 having a length 147 substantially equal to an inner diameter of the chamber 114 such that the bobbin 140 may be press-fitted into the chamber 114 to thereby secure the bobbin 140 to the housing 108. The first end plate 144 includes a threaded portion 148. The threaded portion 148 is similar to the threaded portion 112 and may be configured to be mated with a threaded aperture defined in the stem 104. Similar to the bobbin 118 described above in regard to FIGS. 5a and 5b, the bobbin 140 is positioned and secured in the chamber 114 of the housing 108 such that the reference plane 120 formed from the coil turns of the secondary coil 116 are substantially parallel with the sagittal plane 80 of the patient 54 when the tibial tray 100 is properly implanted in the patient 54. Again, in such a configuration, when the patient 54 passes through the passageway 78 of the gate 70 as illustrated in FIG. 3, the reference plane 120 defined by the coil turns of the secondary coil 116 of the orthopaedic implant 52 (e.g., the tibial tray 100) is substantially parallel with the reference planes 82, 84 defined by the coil turns of the primary/receiver coils 50.

Although the secondary coil 116 has been described above in regard to several illustrative embodiments, it should be appreciated that in other embodiments the secondary coil 116 may be embodied as any type of coil capable of receiving power from a primary coil (e.g., the primary coils 50). For example, the secondary coil 116 may be embodied as a radio frequency identification (RFID) coil. In such embodiments the RFID coil may be positioned in the chamber 114 of the housing 108 or, alternatively, secured to the orthopaedic implant 52 (e.g., the tibial tray 100) in any location such that a reference plane defined by the coil turns of the RFID coil is substantially parallel with the sagittal plane 80 of the patient 54 when the orthopaedic implant 52 is properly implanted in the patient 54.

Figure 6:
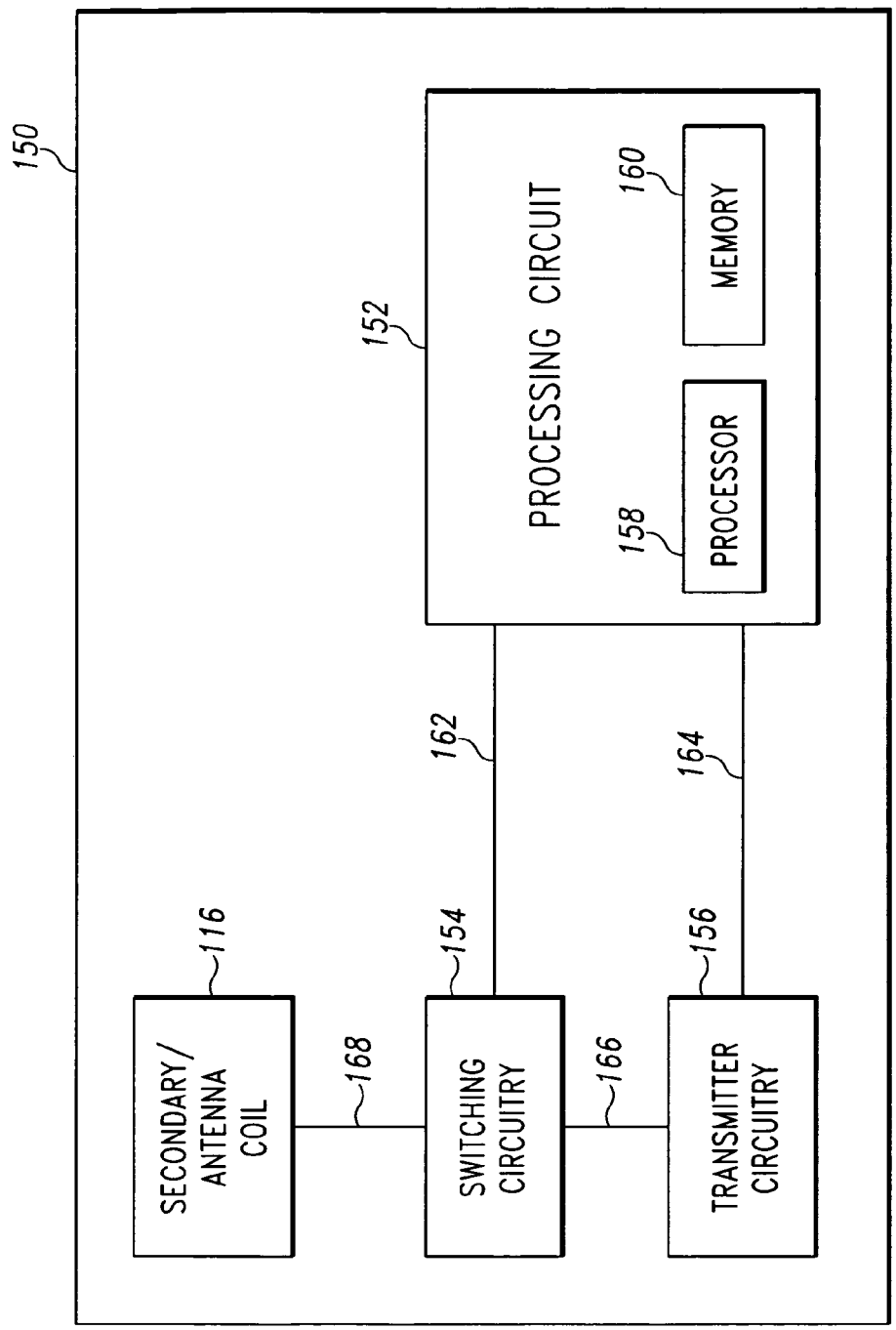
FIG. 6 is a simplified block diagram of an electrical circuit of the orthopaedic implant of FIGS. 4 and 5a-5d.

Referring now to FIG. 6, in one embodiment, the secondary coil 116 forms a portion of an electronic circuit 150, which is included in the orthopaedic implant 52 (e.g., the tibial tray 100). The electronic circuit 150 is secured to the orthopaedic implant 52 in a location such that the electronic circuit 150 is not adversely affected by bodily tissue or fluid and does not adversely affect the structural integrity of the orthopaedic implant 52. For example, in embodiments wherein the orthopaedic implant 52 is embodied as the tibial tray 100, the electronic circuit 150 may be positioned in the chamber 114 of the housing 108 and secured to the housing 108 in a manner similar to the bobbin 118. Additionally or alternatively, a portion of the electronic circuit 150 may be positioned in the stem 104 and/or platform 102 of the tibial tray 100.

The circuit 150 also includes a processing circuit 152, switching circuitry 154, and transmitter circuitry 156. The processing circuit 152 may be embodied as any type of processing circuit and may include any number of electronic devices. Illustratively, the processing circuit 152 includes a processor 158 and a memory device 160. The processor 158 may be embodied as any type of processor including, for example, discrete processing circuitry (e.g., a collection of logic devices), general purpose integrated circuit(s), and/or application specific integrated circuit(s) (i.e., ASICS). The memory device 160 may be embodied as any type of memory device and may include one or more memory types, such as, random access memory (i.e., RAM) and/or read-only memory (i.e., ROM). Illustratively, the implant identification data is stored in the memory device 160. The switching circuitry 154 may be embodied as any collection of electrical and/or mechanical device capable of selectively connecting the secondary coil 116 to the transmitter circuitry 156 or the processing circuit 152. The transmitter circuitry 156 may be embodied as any type of transmitter circuitry capable of transmitting the implant identification data from the orthopaedic implant 52 to the primary/receiver coil 50 or other receiver. For example, the transmitter circuitry 156 may be embodied as an inductor-capacitor (LC) circuit, a resonating crystal circuit, or the like. The transmitter circuitry 156 may use any carrier frequency capable of transmitting the identification data. In one particular embodiment, the transmitter circuitry 156 is configured to transmit the implant identification data using a low carrier frequency such as, for example, a frequency of about 125 kilohertz to about 143 kilohertz or from about 13.553 megahertz to about 13.567 megahertz. However, it should be appreciated that in other embodiments, other frequencies may be used by the transmitter circuitry 156 to transmit the implant identification data.

The processing circuit 152 is communicatively coupled to the switching circuitry 154 via a number of communication links 162 and to the transmitter circuitry 156 via a number of communication links 164. The switching circuitry 154 is communicatively coupled to the transmitter circuitry 156 via a number of communication links 166 and to the secondary coil 116 via a number of communication links 168. The communication links 162, 164, 166, 168 may be any type of communication links capable of providing communication between the processing circuit 152, the switching circuitry 154, the transmitter circuitry 156 and the secondary coil 116. For example, the communication links may be embodied as any number of wires, cables, fiber optic cables, printed circuit board traces, vias, or the like.

In use, when the secondary coil 116 is inductively coupled to the primary coil 50, an amount of energy is transferred to the secondary coil 116. The switching circuitry 154 connects the secondary coil 116 to the processing circuit 152 (i.e., the communication links 168 and 162 are electrically connected to each other) to thereby power the processing circuit 152. In response to the power signal received from the secondary coil 116, the processing circuit 152 controls the switching circuitry 152 to connect the transmitter circuitry 156 to the secondary coil 116 (i.e., the communication links 166 and 168 are electrically connected to each other). The processing circuit 152 subsequently controls the transmitter circuitry 156 to transmit the implant identification data using the secondary coil 116 as a transmitter coil.

Figure 7:
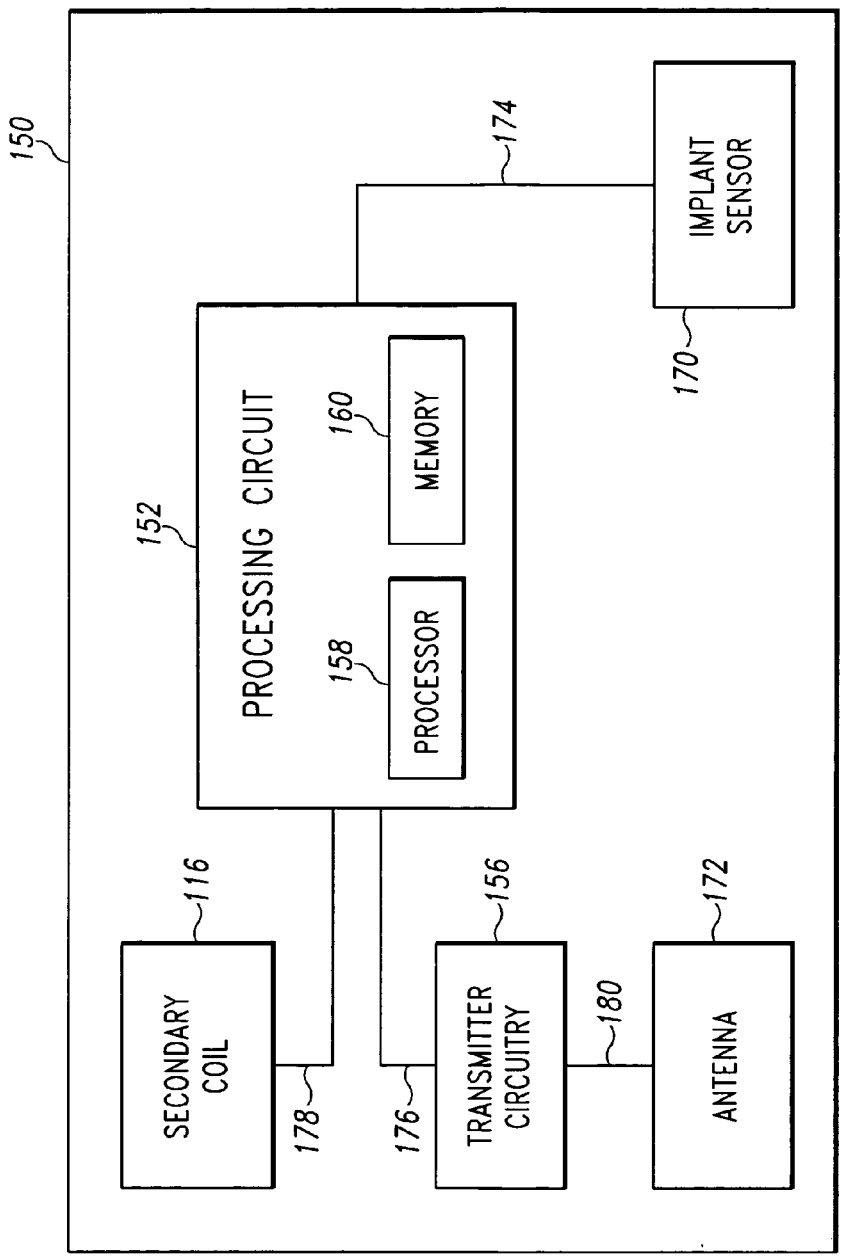
FIG. 7 is a simplified block diagram of another embodiment of the electrical circuit of FIG. 6.

Referring now to FIG. 7, in another embodiment, the electronic circuit 150 may include one or more implant sensors 170 and a separate antenna 172. The implant sensors 170 may be any type of sensors such as, for example, pressure sensors, load sensors, temperature sensors, strain sensors, hall-effect sensors, or the like. The implant sensors 170 may be secured to the orthopaedic implant 52 or may be positioned remotely therefrom. The antenna 172 may be embodied as any type of antenna usable by the transmitter circuitry 156 to transmit the implant identification data and implant sensor data produced by the implant sensors 170. In one embodiment, the antenna 172 is embodied as a monopole antenna positioned so as to extend beyond the metal portion of the orthopaedic implant 52. For example, the antenna 172 may be embedded in a plastic portion of the orthopaedic implant 52 such as a bearing surface or the like. Alternatively, a metal portion of the orthopaedic implant 52 may be used as the antenna 172 as described in U.S. patent application Ser. No. 10/880,003, entitled "System and Method for Bidirectional Communication with an Implantable Medical Device using an Implant Component as an Antenna", which was filed on Jun. 29, 2004 by Jason T. Sherman et al., the entirety of which is incorporated herein by reference.

The processing circuit 152 is communicatively coupled to the implant sensors 170 via a number of communication links 174. The processing circuit 152 is also coupled to the transmitter circuitry 156 via a number of communication links 176 and to the secondary coil 116 via a number of communication links 178. The transmitter circuitry 156 is also coupled to the antenna 172 via a number of communication links 180. The communication links 174, 176, 178, 180 may be any type of communication links capable of providing communication between the processing circuit 152, the implant sensors 170, the transmitter circuitry 156, the antenna 172, and the secondary coil 116.

In such embodiments, the processing circuit 152 is configured to receive power from the secondary coil 116 when the secondary coil 116 is inductively coupled to the primary coil 50 (e.g., when the patient 54 is walking through the passageway 78 of the gate 70) or to an alternative primary coil (e.g., a portable primary coil usable by a surgeon to retrieve implant sensor data at any location such as in an examination room). In response to a power signal received from the secondary coil 116, the processing circuit 152 is configured to receive an output signal(s) from the implant sensors 170 and transmit the output signal(s) and the implant identification data, which may be retrieved from the memory device 160, using the transmitter circuitry 156 and the antenna 172. In some embodiments, such as those embodiments wherein the implant sensors 170 are magnetic-type sensors such as Hall-effect sensors, the processing circuit 152 may be configured to wait until the primary coil 50 has been deactivated or the orthopaedic implant 52 is otherwise not affected by an electromagnetic field prior to accepting or taking measurements from the implant sensors 170.

In embodiments wherein the electronic circuit 150 includes one or more implant sensors 170, the transmitter circuitry 156 may be configured to transmit the implant identification data and the implant sensor data using a higher frequency than those embodiments wherein an implant sensor 170 is not included due to the increase in the overall amount of data transferred in the allotted time. For example, the transmitter circuitry 156 may be configured to transmit the implant identification data and the implant sensor data using a carrier frequency of about 2.4 gigahertz to about 2.483 gigahertz. However, it should be appreciated that in other embodiment, other high frequencies may be used by the transmitter circuitry 156 to transmit the implant identification data and the implant sensor data.

Figure 8:
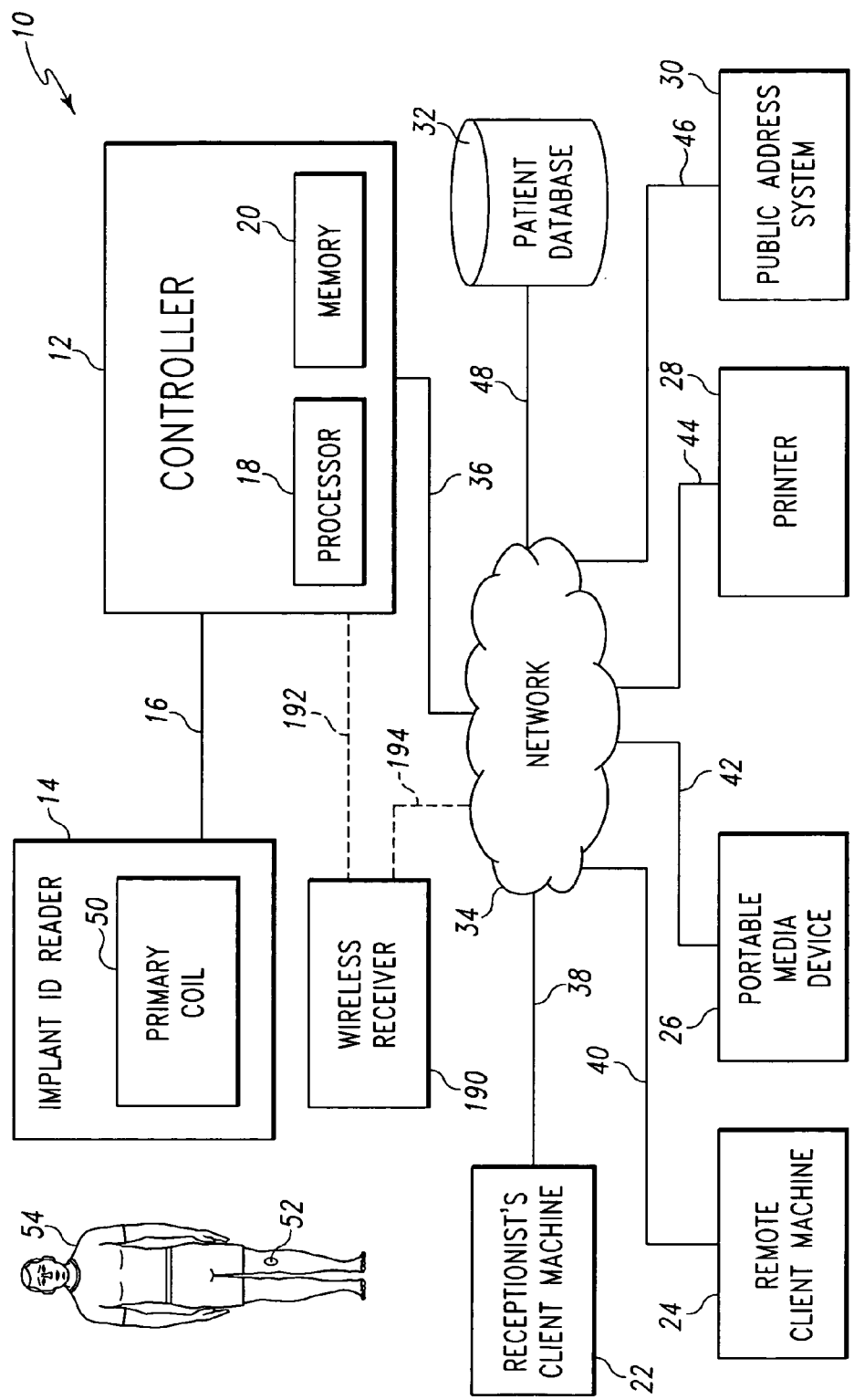
FIG. 8 is a simplified block diagram of another embodiment of the system of FIG. 1.

Referring now to FIG. 8, in another embodiment, the network 34 of the system 10 may be embodied as a wireless network such as a wireless local area network (WLAN). In such embodiments, the system 10 may include a wireless receiver 190. The wireless receiver 190 may be embodied as any type of wireless receiver capable of receiving the identification data and implant sensor data from the orthopaedic implant 52. For example, the wireless receiver may be embodied as a wireless router. In such embodiments, the transmitter circuitry 156 of the orthopaedic implant 52 is configured to transmit the implant identification data and the implant sensor data, if available, using the frequency of the wireless network. For example, in one particular embodiment, the transmitter circuitry 156 is configured to transmit the implant identification data and the implant sensor data using a carrier frequency in the 2.4 gigahertz unlicensed band (e.g., using a carrier frequency in the range of about 2.4 gigahertz to about 2.483 gigahertz). Additionally or alternatively, in some embodiments, the transmitter circuitry 156 may be configured to transmit the implant identification data and the implant sensor data using a Bluetooth transmission protocol. Regardless, the wireless receiver 190 is configured to receive the implanted identification data and the implant sensor data, if available, transmitted by the orthopaedic implant 52.

The wireless receiver 190 may be communicatively coupled to the controller 12 via a number of communication links 192 such as wires, cables, or the like. Alternatively, in embodiments wherein the wireless receiver 190 is a wireless router, the receiver 190 may be communicatively coupled to the controller 12 via a wireless communication link 194 and the wireless network 34.

Figure 9:
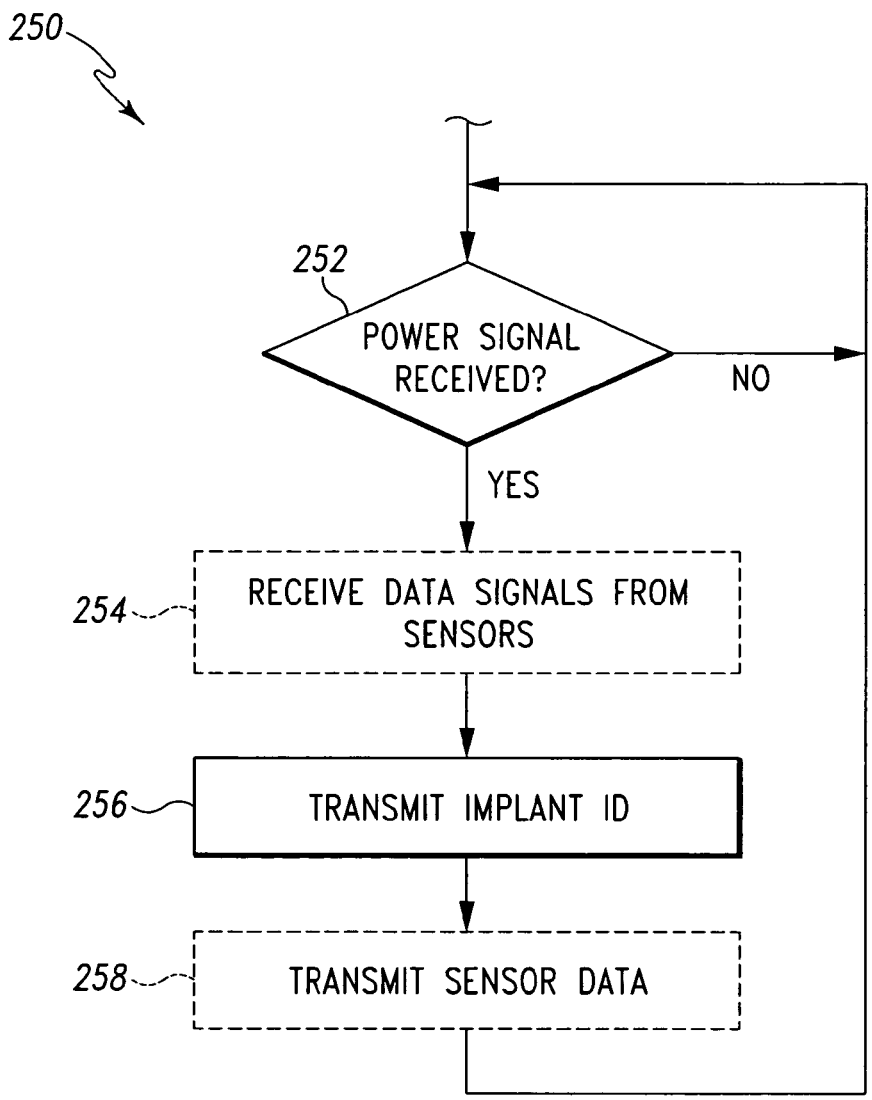
FIG. 9 is a simplified flowchart of an algorithm for transmitting implant data that is executed by the electrical circuits of FIGS. 6 and/or 7.

In operation, the electronic circuits 150 of the orthopaedic implants 52 may execute an algorithm 250 for transmitting implant data as illustrated in FIG. 9. The algorithm 250 begins with a process step 252 in which the processing circuit 152 of the circuit 150 activates when a power signal has been received from the secondary coil 116 via the communication links 168, 162 or 178. In embodiments wherein the circuit 50 includes a number of implant sensors 170, the algorithm 250 advances to process step 254 when a power signal has been received. In process step 254 the processing circuit 152 receives output data from the implant sensors 170 via the communication link 174. Depending on the type of the implant sensors 170, the output data may be, for example, pressure data, temperature data, or the like.

Subsequently, in process step 256, the processing circuit 152 transmits the implant identification data. To do so, the implant identification data may be retrieved from the memory device 160. As discussed above in regard to FIG. 1, the implant identification data may be embodied as a code or password, which is digitally stored in the memory device 160. In embodiments wherein the secondary coil 116 is also used as an antenna coil (FIG. 6), the processing circuit 152 also controls the switching circuitry 154 to connect the transmitter circuitry 156 to the secondary coil 116 in process 256. The implant identification data is subsequently transmitted by the circuitry 150 using the transmitter circuitry 156 and the secondary coil 116 as an antenna coil. Alternatively, in embodiments wherein the circuitry 150 includes a separate antenna 172 (FIG. 7), the processing circuitry 152 controls the transmitter circuitry 156 to transmit the implant identification data using the antenna 172.

Once the implant identification data has been transmitted in process step 256, the output signals received from the implant sensors 170 is transmitted in process step 258. To do so, the processing circuitry 152 controls the transmitter circuitry 156 to transmit the implant identification data using the antenna 172. Once the implant identification data and the output signals from the implant sensors 170, if any, have been transmitted, the algorithm 250 loops back to process step 252 in which the processing circuit 252 determines if another power signal has been received or is still being received from the secondary coil 116. In this way, the electronic circuit 150 is configured to periodically transmit the implant identification data (and implant sensor data) while secondary coil is indicatively coupled to the primary coil. That is, while the patient 54 is walking though or standing in the passageway 78 of the gate 70, the electronic circuit 150 of the orthopaedic implant 52 will transmit the implant identification data and the output signals from the implant sensors 170 if available.

Figure 10:
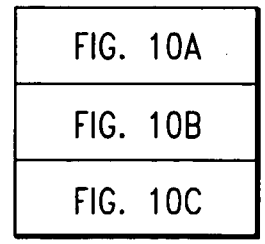
FIG. 10 is a simplified flowchart of an algorithm for managing patient-related data that is executed by the systems of FIGS. 1 and/or 8.

In use, the system 10 may execute an algorithm 300 for managing patient-related data as illustrated in FIG. 10. The algorithm 300 begins with a process step 302 in which the primary coil 50 of the implant identification reader 14 (e.g., the gate 70) is inductively coupled with the secondary coil 116 of the orthopaedic implant 52. To do so, the controller 12 is configured to transmit a power signal to the primary coil 50 via the communication link 16 to thereby energize the coil 50. In response the primary coil 50 generates an electromagnetic field, which is received by the secondary coil 116 of the orthopaedic implant 52. It should be appreciated that the controller 12 may be configured to continuously energize the primary coil 50, periodically energize the primary coil 50, or selectively energize the primary coil 50. For example, in some embodiments, the implant identification reader 14 may include a pressure or motion sensor configured to determine the presence of the patient 54. In such embodiments, the pressure, motion, or other sensor output is transmitted to the controller 12 and, in response, the controller 12 transmits the power signal to the primary coil 50. In this way, the primary coil 50 is only energized when a patient 54 is present such as when a patient 54 is walking through or standing in the passageway 78 of the gate 70.

Once the power signal has been transmitted to the power coil 50, the controller 12 determines if any implant identification data is available (i.e., if any implant identification data is being transmitted) in process step 304. If not, the algorithm 300 loops back to the process step 302 wherein the controller 12 continuously, periodically, or selectively transmits the power signal to the primary coil 50. However, if implant identification data is being transmitted by the orthopaedic implant 54, the algorithm 300 advances to process step 306. In process step 306, the implant identification data is received from the orthopaedic implant. To do so, in embodiments wherein the primary coil 50 is also a receiving coil (FIG. 1), the implant identification data is received by the primary/receiving coil 50 and transmitted to the controller 12 via the communication link 16. However, in embodiments wherein the system 10 includes the wireless receiver 190 (FIG. 8), the implant identification data is received by the wireless receiver 190 and transmitted to the controller 12 via the communication link 192 or via the communication link 194, the wireless network 34, and the communication link 36.

Similarly, in embodiments wherein the orthopaedic implant 52 includes the number of implant sensors 170, the controller 12 receiving implant sensor data transmitted by the orthopaedic implant 52 in process step 308. The controller 12 may receive the implant sensor data in a manner similar to the implant identification data. That is, in embodiments wherein the primary coil 50 is also a receiving coil (FIG. 1), the implant sensor data is received by the primary/receiving coil 50 and transmitted to the controller 12 via the communication link 16. Alternatively, in embodiments wherein the system 10 includes the wireless receiver 190 (FIG. 8), the implant sensor data is received by the wireless receiver 190 and transmitted to the controller 12 via the communication link 192 or via the communication link 194, the wireless network 34, and the communication link 36.

Once the implant identification data (and implant sensor data) has been received by the controller 12, the algorithm 300 advances to process step 310. In process step 310, the controller 12 receives security code data. The security code data may be entered automatically or manually and may be embodied as any type of security code data such as a password, digital code, or other data. For example, in some embodiments the security code data is embodied as a digital code stored in a keyfob or the like that may be passed in front of a code reader (not shown) to thereby transmit the security code data. Alternatively, the security code data may be embodied as a digital fingerprint or the like, which is entered via a digital fingerprint analyzer. The security code data may be entered directly into the controller 12 or, in some embodiments, is entered via one of the receptionists client machines 22. In such embodiments, the controller 12 communicates with the client machine 22 to request that the security code data be entered. For example, a prompt may be displayed on a display of the client machine 22. In response, a receptionist, nurse, or other caregiver may be enter a password, swipe a keyfob having the digital security data stored therein, or press a finger on a digital fingerprint analyzer coupled to the client machine 22. Regardless of the type of security code data entered, the client machine 22 transmits the security code data to the controller 12 via the combination link 38, the network 34 and the communication link 36. Alternatively or additionally, in some embodiments, the patient 54 is requested to enter security code data such as a password, personal identification number, or the like. The patient 54 may enter the security code data via a client machine or the like located in the waiting area of the doctor's office or hospital wherein the system 10 is incorporated.

Once the controller 12 has received the security code data, the controller 12 determines if the security code data is valid in process step 312. To do so, the controller 12 may retrieve a security code list or the like from the database 32 and compare the received security code data to one or more of the security codes retrieved from the database 32. If the security code data is not valid, the algorithm 300 loops back to the process step 310 wherein the controller 12 waits for additional security code data to be entered. If, however, the security code data is valid, the controller 12 advances to process step 314 wherein patient-related data is retrieved from the database 32. To do so, the controller 12 accesses the database 32 via the communication links 36, the network 34, and the communication link 48 and retrieves the patient-related data that is associated with the implant identification data received in process step 306. That is, the patient-related data is stored in the database 32 in association with or indexed by the implant identification data. The controller 12 accesses the appropriate patient-related data based on implant identification data. In this way, the patient-related data is only retrieved if the security code data has been entered and is valid.

Once the patient-related data has been retrieved in process step 314, the controller 12 determines if any of the patient-related data requires updating. For example, the controller 12 may determine if any of the patient-related data is missing such as the patient's 54 address or the like. Additionally or alternatively, the controller 12 may determine that the patient-related data requires updating if a portion, such as the patient's 54 address, has not been updated for a predetermined period of time. If the patient-related data does require updating, the controller 12 is configured to retrieve an electronic patient information form from the database 32 in process step 318. The patient information form includes a number of data fields wherein the patient 54 may supply patient-related information such as address information, insurance information, or the like. In addition, the controller 12 may be configured to populate a portion of the electronic form with the patient-related data. For example, the controller 12 may populate the name and address data fields of the electronic form with the name and address information included in the patient-related data that was retrieved in process step 314.

Once the electronic patient information form has been retrieved and populated in process step 318, the algorithm 300 advances to process step 320. In process step 320, the controller 12 transmits the populated electronic form to the printer 28 via the communication link 36, the network 34, and the communication link 44. In response, the printer 28 prints a "hard copy" of the electronic patient information form so that the patient 54 may supply any required patient information. Once the patient 54 has filled out the printed patient information form, the patient information supplied by the patient 54 on the form may be entered into the system 10. To do so, in one embodiment, a receptionist, nurse, or other caregiver may manually enter the data from the patient information form into one of the receptionist's client machines 22. In response, the client machine 22 transmits the information to the controller 12 via the communication link 38, the network 34, and the communication link 36. In response to the new patient information, the controller 12 is configured to update the patient-related data with the new patient information by accessing the database 32 and storing the updated or new patient information in the database 32.

In other embodiments, the patient-related data may be updated electronically without the use of a printed form. In such embodiments, the controller 12 is configured to transmit the retrieved (and populated) electronic form to, for example, an electronic tablet or other data entry device usable by the patient 54. The controller 12 may transmit the electronic form using a wireless or wired signal depending on the type of data entry device used. The patient 54 may then personally update the patient-related data and/or provide additional patient data. Once complete, the controller 12 may be configured to receive the updated patient information from the electronic tablet or data entry device and update the patient-related data with the new patient information. In this way, the updating of the patient-related information is automated and a nurse or receptionist is not required to manually enter the new patient information from a printed form.

Referring back to process step 316, if the patient-related data does not required updating, the algorithm 300 advances to process step 324. In process step 324, the controller 12 is configured to update a patient queue with the name of the patient 54 as determined by the patient-related data in process step 314. That is, the controller 12 is configured to extract the name of the patient 54 from the patient-related data and add the patient's name to the bottom of the patient queue (if the patient queue is a first in-first out type of queue). The patient queue may be stored on, for example, one or more of the receptionists client machines 22 such that the receptionist may monitor and adjust the patient queue. Once the patient queue has been updated with the patient 54, the controller 12 determines if a patient room is available in process step 326. To do so, the controller 12 may monitor the patient queue and subtract patient's names from the queue as patient rooms are assigned to the patients. The controller 12 may also be configured to adjust the patient queue based on specific patient rooms, medical equipment located therein, and/or other parameters. For example, if a specific patient room is used for particular types of examinations or surgical procedures, the controller 12 may be configured to adjust the queue such that the particular patient room is assigned to the patient scheduled for such examination or procedure. Additionally, if the examination or medical procedure requires particular medical equipment, the controller 12 may be configured to adjust the patient queue such that the patient room wherein the particular medical equipment is located is assigned to the patient scheduled for such examination or procedure.

Once the patient's 54 name is at the top of the patient queue and a room is available, the algorithm 300 advances to process step 328. In process step 328, the controller 12 is configured to notify the receptionist that a patient room is available for the patient 54. To do so, the controller 12 may transmit an electronic signal or notification to one or more of the receptionist's client machines 22. Once so notified, the receptionist may notify the patient 54 and escort the patient 54 to the assigned patient room. Additionally, in some embodiments, the controller 12 is configured to activate the public address system 30 to notify the patient that a patient room is available in process step 330. To do so, the controller 12 transmits data to the public address system 30 via the communication link 36, the network 34, and the communication link 46. For example, in embodiments wherein the public address system 30 is embodied as display device, the controller 12 is configured to transmit the patient's 54 name and patient room number to the public address system 30 to cause the patient's 54 name and patient room number to be displayed to the patient 54.

Once the receptionist and patient has been notified that a patient room is available, the algorithm 300 advances to process step 332. In process step 332, the controller 12 is configured to transmit the patient-related data to the remote client machine 24 associated with the patient room assigned to the patient 54. For example, in embodiments wherein the remote client machines 24 is located in the patient rooms, the controller 12 is configured to transmit the patient-related data to the remote client machine located in the patient room that has been assigned to the patient 54. The controller 12 may transmit the patient-related data to the remote client machine 24 via the communication links 36, the network 34, and the communication links 40. In addition, the controller 12 transmits patient-related data to the portable media device 26 used by the doctor or caregiver that is to examine or operate on the patient 54. The controller 12 may transmit the patient-related data to the portable media device 26 via the communication links 36, the network 34, and the communication links 42. In this way, the doctor or caregiver may review, update, and supply new patient-related data via the remote client machine 24 located in the patient room or the portable media player prior to, during, or after the patient examination and/or surgery. In embodiments wherein the orthopaedic implant 52 is configured to transmit implant sensor data, the controller 12 is also configured to transmit the implant sensor data to the remote client machine 24 and the portable media device 26 in process step 334.

Once the patient-related data and implant sensor data, if available, has been transmitted to the remote client machine 24 and the portable media device 26, the algorithm 300 determines if the patient appointment is completed in process step 336. To do so, the controller 12 may monitor the remote client machine 24 located in the assigned patient room and/or the portable media device 26 for notification from the doctor or caregiver that the appointment is complete. If so, the algorithm 300 advances to process step 338 wherein the controller 12 receives any new or updated patient-related information entered by the doctor or caregiver prior to, during, or subsequent to the examination or surgery. For example, during the examination, the doctor may enter notes into the client machine 24 located in the patient room and/or the doctor's portable media device 26. It should be appreciated that any type of data may be supplied to the client machine 24 and/or portable media device 26 prior to, during, or subsequent to the patient examination or surgery. For example, caregiver notes, prescriptions, patient symptoms, X-rays, or the like may be recorded. Regardless, once the appointment is complete any data entered by the doctor or other caregiver is transmitted to the controller 12 in process step 338.

Subsequently, in process step 340, the controller 12 is configured to update the patient database 32 with the new patient-related data received in process step 338. To do so, the controller 12 transmits the new patient-related data to the database 30 via the communication links 36, the network 34, and the communication links 48. The new patient-related data is stored in the database 30 in association with the implant identification data received in process step 306.

Once any new patient-related data is stored in process step 340, the controller 12 schedules the patient 54 for a next appointment in process step 342. To do so, the controller 12 may be configured to transmit a notification to one of the receptionist's client machines 22 that a follow-up appointment is required. The receptionist may then communicate with the patient 54 to schedule the next appointment. Alternatively, if the doctor or caregiver has already supplied a date for the next appointment, the controller 12 may automatically schedule patient 54 for the appointment. For example, the controller 12 may be configured to enter the patient's 54 name, as determined from the patient-related data retrieved in process step 306, into an electronic calendar, which may be viewable on one or more of the receptionist's client machines 22. In addition, a confirmation of the scheduled appointment may be printed on the printer 28 for the patient's 54 records.

Figure 10A:
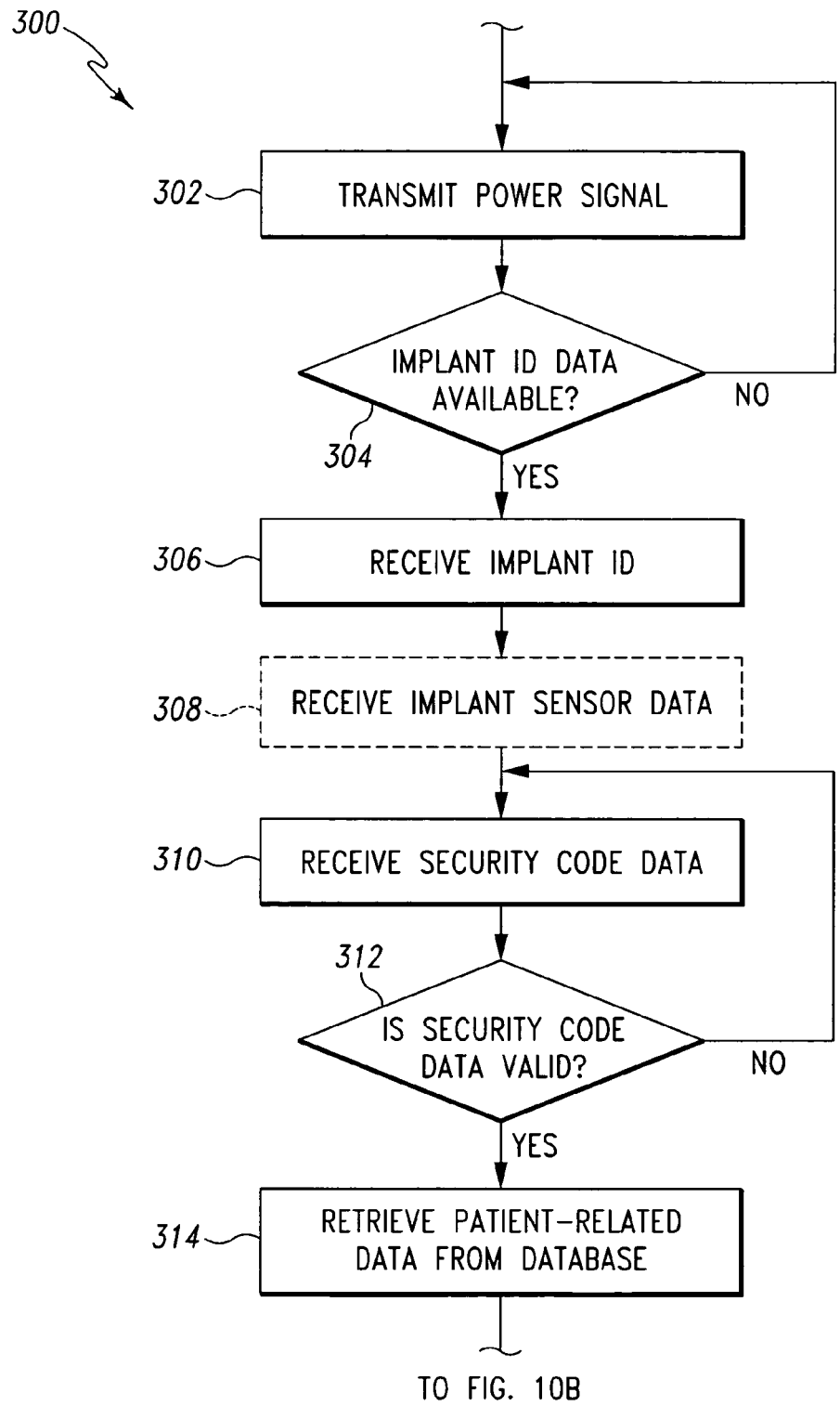
Figure 10B:
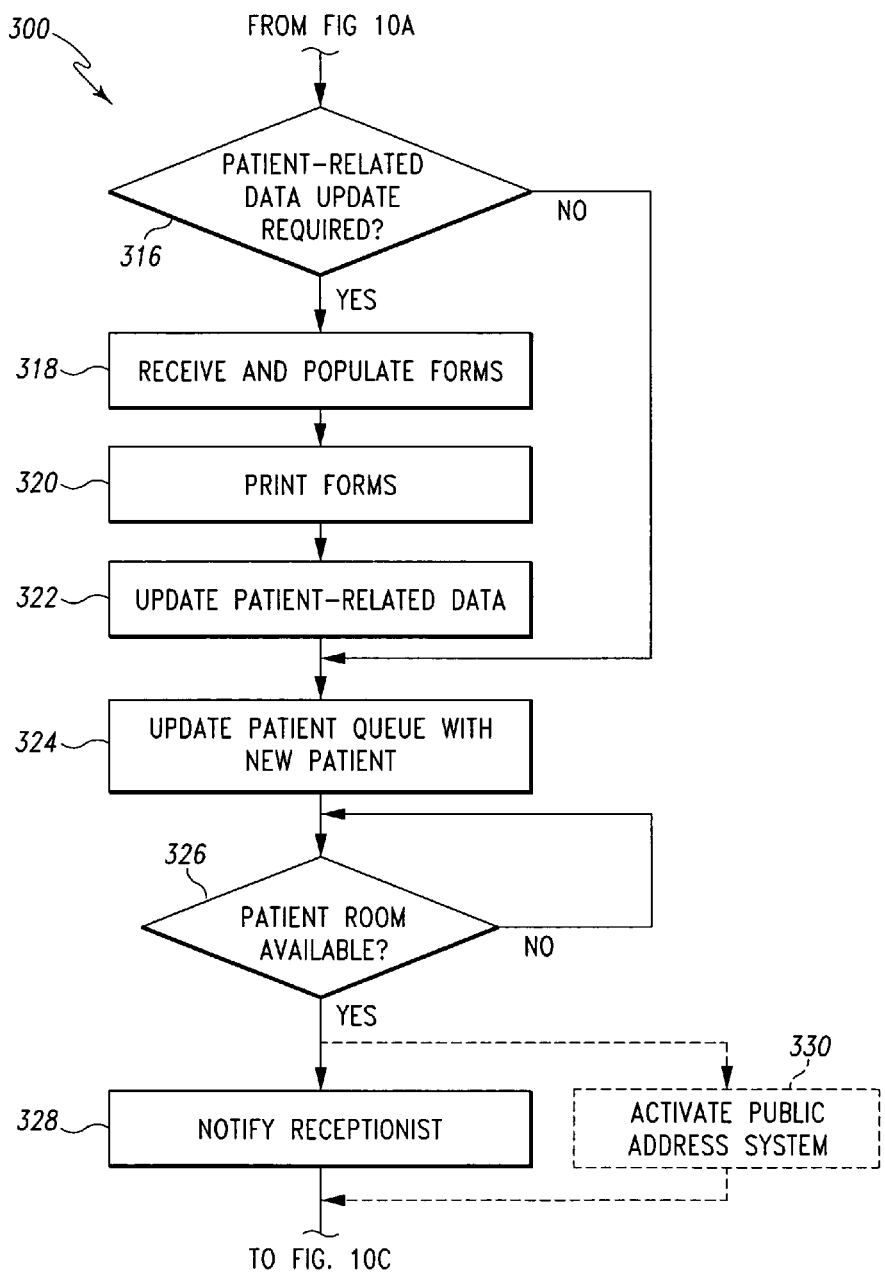
Figure 10C:
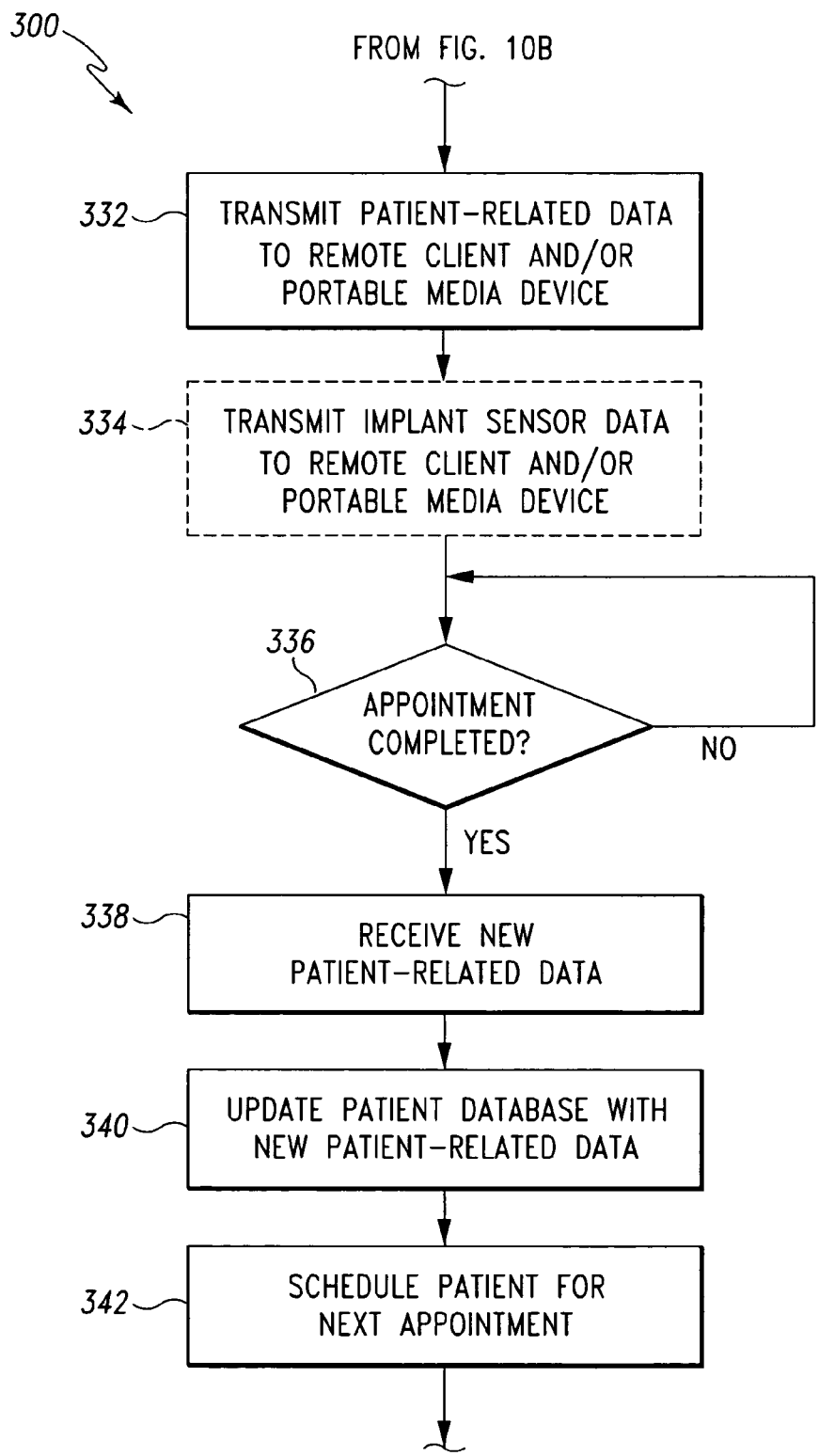

Although the process steps of the algorithm 300 are illustrated in FIGS. 10a-10c according to a particular sequential order, it should be appreciated that many of the process steps may be performed in any order and/or performed contemporaneously with each other. For example, the patient queue may be updated with the new patient prior to determining if the retrieved patient-related data requires updating rather than subsequent thereto. Additionally, although the orthopaedic implant 52 has been described as a tibial tray in one illustrative embodiment, it should be appreciated that in other embodiments the orthopaedic implant 52 may be embodied as any type of orthopaedic implant. For example, the orthopaedic implant 52 may be embodied as femoral orthopaedic implant, a hip joint orthopaedic implant, a shoulder joint orthopaedic implant, or the like.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. An orthopaedic implant comprising:
a housing having a chamber defined therein;
a bobbin positioned in the chamber, the bobbin having a plurality of apertures positioned along an axis extending in a medial-lateral direction; and
a secondary coil positioned in the chamber of the housing and having a plurality of coil turns about a longitudinal axis each coil turn of the plurality of coil turns of the secondary coil (i) passing through a separate corresponding aperture of the plurality of apertures of the bobbin, and (ii) being positioned in a corresponding reference plane extending in an anterior-posterior direction orthogonal to the longitudinal axis,
wherein when the orthopaedic implant is implanted in a patient (i) the corresponding reference planes are capable of being oriented substantially parallel with a sagittal plane of a body of the patient and (ii) the longitudinal axis is capable of being oriented substantially orthogonal to the sagittal plane of the body of the patient.

2. An orthopaedic implant comprising
a platform having a bottom surface;
a stem secured to the bottom surface of the platform and extending downwardly therefrom;
a housing coupled to the stem having a chamber defined therein;
a bobbin positioned in the chamber, the bobbin including an end plate having an upper surface extending parallel to the bottom surface of the platform in a medial-lateral direction; and
a secondary coil positioned in the chamber of the housing and having a plurality of coil turns about a longitudinal axis, each coil turn of the plurality of coil turns of the secondary coil being positioned in a corresponding reference plane extending in an anterior-posterior direction orthogonal to the upper surface of the end plate,
wherein when the orthopaedic implant is implanted in a patient (i) the corresponding reference planes are capable of being oriented substantially parallel with a sagittal plane of a body of the patient and (ii) the longitudinal axis is capable of being oriented substantially orthogonal to the sagittal plane of the body of the patient.

3. An orthopaedic implant comprising:
a platform having a bottom surface;
a stem secured to the bottom surface of the platform and extending downwardly therefrom;
a housing coupled to the stem having a chamber defined therein; and
a secondary coil having a plurality of coil turns in registry with each other about a longitudinal axis, the longitudinal axis extending in a first direction parallel to the bottom surface of the platform, each coil turn of the secondary coil being positioned in a corresponding reference plane extending orthogonal to the longitudinal axis,
wherein the secondary coil is positioned in the chamber of the housing such that (i) the corresponding reference planes are capable of being oriented substantially parallel with a sagittal plane of a body of a patient and (ii) the longitudinal axis is capable of being oriented substantially orthogonal to the sagittal plane of the body of the patient when the orthopaedic implant is implanted in the patient and the patient is in a standing position.

4. The orthopaedic implant of claim 3, wherein the orthopaedic implant is a tibial tray.

5. The orthopaedic implant of claim 3, further comprising a processing circuit electrically coupled to the secondary coil and configured to receive a power signal from the secondary coil when the secondary coil is inductively coupled with a primary coil.

6. The orthopaedic implant of claim 5, further comprising:
a wireless transmitter coupled to the processing circuit; and
an antenna coil electrically coupled to the wireless transmitter,
wherein the processing circuit is configured to control the wireless transmitter to transmit implant identification data in response to the power signal using the antenna coil.

7. The orthopaedic implant of claim 6, wherein the wireless transmitter is configured to transmit the implant identification data at a frequency of about 2.4 gigahertz.

8. The orthopaedic implant of claim 6, wherein the wireless transmitter is configured to transmit the implant identification data using a wireless local area network frequency.

9. The orthopaedic implant of claim 6, wherein the processing circuit and the wireless transmitter are configured to transmit the implant identification data using a Bluetooth transmission protocol.

10. The orthopaedic implant of claim 6, further comprising a sensor electrically coupled to the processing circuit, wherein the processing circuit is configured to:
receive an output signal from the sensor; and
control the wireless transmitter to transmit the output signal in response to the power signal using the antenna coil.

11. The orthopaedic implant of claim 10, wherein the sensor is a sensor selected from the group consisting of a pressure sensor, a load sensor, a temperature sensor, and a hall-effect sensor.

12. The orthopaedic implant of claim 10, wherein the wireless transmitter is configured to transmit the output signal at a frequency of about 2.4 gigahertz.

13. The orthopaedic implant of claim 10, wherein the wireless transmitter is configured to transmit the output signal using a wireless local area network frequency.

14. The orthopaedic implant of claim 10, wherein the processing circuit and the wireless transmitter are configured to transmit the output signal using a Bluetooth transmission protocol.

* * * * *